US007205554B2

(12) United States Patent
Tokuda et al.

(10) Patent No.: US 7,205,554 B2
(45) Date of Patent: Apr. 17, 2007

(54) METHOD AND APPARATUS FOR PROCESSING A MICRO SAMPLE

(75) Inventors: Mitsuo Tokuda, Tachikawa (JP); Muneyuki Fukuda, Kokubunji (JP); Yasuhiro Mitsui, Fuchu (JP); Hidemi Koike, Hitachinaka (JP); Satoshi Tomimatsu, Kokubunji (JP); Hiroyasu Shichi, Nishitokyo (JP); Hideo Kashima, Tokyo (JP); Kaoru Umemura, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/127,213

(22) Filed: May 12, 2005

(65) Prior Publication Data

US 2005/0199828 A1 Sep. 15, 2005

Related U.S. Application Data

(63) Continuation of application No. 10/878,528, filed on Jun. 29, 2004, now Pat. No. 6,927,391, which is a continuation of application No. 09/960,479, filed on Sep. 24, 2001, now Pat. No. 6,781,125.

(30) Foreign Application Priority Data

| Nov. 2, 2000 | (JP) | ............... 2000-340387 |
| Nov. 7, 2000 | (JP) | ............... 2000-344226 |

(51) Int. Cl.
*H01J 37/256* (2006.01)
*G21N 23/225* (2006.01)
(52) U.S. Cl. ............... 250/492; 250/492.21; 250/492.3
(58) Field of Classification Search ............. 250/492.3, 250/492.21
See application file for complete search history.

(56) References Cited

U.S. PATENT DOCUMENTS 4,476,386 A 10/1984 Reid et al. ................. 250/310

(Continued)

FOREIGN PATENT DOCUMENTS

EP 0 927 880 7/1998

(Continued)

OTHER PUBLICATIONS

Ohnishi, T., et al.: *A new focused-ion-beam microsampling technique for TEM observation of site-specific areas*. ISTFA '99. Proceedings of the 25TH International Symposium for Testing and Failure Analysis. ASM Int. 1999, pp. 449-453 (Nov. 14-18, 1999). Materials Parks, OH, USA.

(Continued)

*Primary Examiner*—Frank G. Font
*Assistant Examiner*—James P. Hughes
(74) *Attorney, Agent, or Firm*—Kenyon & Kenyon LLP

(57) ABSTRACT

An object of the invention is to realize a method and an apparatus for processing and observing a minute sample which can observe a section of a wafer in horizontal to vertical directions with high resolution, high accuracy and high throughput without splitting any wafer which is a sample. In an apparatus of the invention, there are included a focused ion beam optical system and an electron optical system in one vacuum container, and a minute sample containing a desired area of the sample is separated by forming processing with a charged particle beam, and there are included a manipulator for extracting the separated minute sample, and a manipulator controller for driving the manipulator independently of a wafer sample stage.

5 Claims, 21 Drawing Sheets

U.S. PATENT DOCUMENTS

| | | | |
|---|---|---|---|
| 5,093,572 A | 3/1992 | Hosono | 250/310 |
| 5,270,552 A | 12/1993 | Ohnishi et al. | 250/307 |
| 5,525,806 A | 6/1996 | Iwasaki et al. | 250/310 |
| 5,633,502 A | 5/1997 | Fischione | 250/441.11 |
| 5,852,298 A | 12/1998 | Hatakeyama et al. | 250/492.2 |
| 6,039,000 A | 3/2000 | Libby et al. | 250/310 |
| 6,300,631 B1 | 10/2001 | Shofner | 250/310 |
| 6,420,722 B2 | 7/2002 | Moore et al. | 250/559.27 |
| 6,538,254 B1 | 3/2003 | Tomimatsu et al. | 250/442.11 |
| 6,717,156 B2 * | 4/2004 | Sugaya et al. | 250/440.11 |
| 2003/0183776 A1 | 10/2003 | Tomimatsu et al. | 250/442.11 |
| 2004/0129897 A1 * | 7/2004 | Adachi et al. | 250/492.3 |
| 2004/0246465 A1 * | 12/2004 | Iwasaki et al. | 356/36 |

FOREIGN PATENT DOCUMENTS

| | | |
|---|---|---|
| JP | 09-326425 | 12/1997 |
| JP | 11-108813 | 4/1999 |
| JP | 10-013945 | 6/1999 |
| JP | 11-260307 | 9/1999 |
| JP | 2000-146780 | 5/2000 |
| JP | 2000-251820 | 9/2000 |
| WO | WO99/05506 | 2/1999 |
| WO | WO99/17103 | 4/1999 |

OTHER PUBLICATIONS

Pawley, James B.,: *A Dual Needle Piezoelectric Micromanipulator for the Scanning Electron Microscope*. The Review of Scientific Instruments, vol. 43, No. 4, Apr. 1972.

R. Weiland et al.: *Wafer Conserving Full Range Construction Analysis for IC Fabrication and process Development Based on FIB/Dual Beam Inline Application*, Proceedings from the 26th International Symposium for Testing and Failure Analysis, Nov. 12-16, 2000, Bellevue, WA, pp. 393-396.

Japanese Office Action 2000-344226.

* cited by examiner

WAFER CONVEYING VEHICLE

METHOD AND APPARATUS FOR PROCESSING A MICRO SAMPLE

This is a continuation of application Ser. No. 10/878,528 filed 29 Jun. 2004, now U.S. Pat. No. 6,927,391 which is a continuation of application Ser. No. 09/960,479 filed 24 Sep. 2001, now U.S. Pat. No. 6,781,125, which claims priority to Japanese Patent Application No. 2000-340387 filed 02 Nov. 2000 and No. 2000-344226 filed 07 Nov. 2000, the contents of which are incorporated herein by reference in their entirety.

BACKGROUND OF THE INVENTION

The present invention relates to an apparatus system used as observation, analysis and evaluation means in research and development and manufacturing of an electronic device such as a semiconductor device, liquid crystal device and a magnetic head, a micro-electronic device or the like which require observation and analysis of not only a surface of an object to be observed but also an inner section near the surface.

In manufacturing of a semiconductor device such as a semiconductor memory typified by a dynamic random access memory, a microprocessor and a semiconductor laser, and electronic parts such as a magnetic head, a product property is inspected for quality control of a product during a manufacturing process or at completion of the process. In the inspection, measurement of manufacturing dimension, defect inspection of a circuit pattern, or analysis of foreign materials are carried out. For that purpose, various means are prepared and used.

Particularly, when there is a wrong portion within the product, a minute processing and observation apparatus is increasingly used which comprises a combination of a focused ion beam (FIB) apparatus and an electron microscope. This apparatus is disclosed in JP-A-11-260307 specification. In the specification, disclosed is a technique of carrying out section processing of a sample by an FIB apparatus and observing an exposed section by an electron microscope disposed slantingly above the sample.

As another technique of observing the sample section, invented and used is a method of taking out of a processing and observation apparatus a minute sample, which is a cut-out minute area of micron orders including an observation region, and moving the minute sample to a separately prepared apparatus to be reprocessed into an optimum shape and observed and analyzed. This method is disclosed in JP-A-5-52721 specification. This is a method of cutting out part of a sample and observing its section, where a tip of a probe driven by a manipulator is positioned on a minute sample cut by an FIB, the probe and minute sample are connected by a deposition gas, and the minute sample is transferred in the connected condition.

SUMMARY OF THE INVENTION

The above described conventional methods have the following problems.

First, to observe a section of a hole or groove of the sample formed by FIB processing, a sample stage is inclined to thereby observe a section of an inner wall of the hole or groove in a slanting direction. In that case, an adjustment range of inclination of the sample stage is limited by constraints in structure due to a working distance of an FIB apparatus, presence of an objective lens, or size of a sample stage, and larger inclination cannot be allowed. Thus, vertical observation of the section of the inner wall of the hole or groove is impossible. The vertical observation of the section is indispensable in confirmation of processing properties such as dry etching, planarization, thin film forming, or the like in process development or the like of semiconductor device manufacturing, but the above described known apparatuses cannot cope with the vertical observation.

Second, a reduction in resolution resulting from the slant observation becomes a serious problem. When slantingly emitting an electron beam to a wafer surface from above and to observe a section of an inner wall of a hole or groove, observation resolution in a direction perpendicular to the wafer surface, that is, of the section of the inner wall of the hole or groove is reduced. A reduction rate reaches approximately 15% at an angle of 30°, and 30% at an angle of around 45°, which is most frequently used. Miniaturization of recent semiconductor devices has reached the limit, and measurement of the dimension or shape with accuracy below a few nano meters is required. Required observation resolution is less than 3 nm, which falls below a technical limit area of a scanning electron microscope. In addition, with high resolution of such degree, depth of focus is extremely shallow and focusing is achieved only in a range below some ten percent of 1 μm, so that an appropriate observation range of a vertical section of the device at the time of slant observation is often less than half of a required area. This problem can be solved by vertical observation. The vertical observation enables superior observation in focus on the whole observation area.

Third, the observation section exists on a wall surface of a minute hole or groove formed in the wafer, so that numeral density of secondary electrons coming out of the hole are reduced in comparison with those on the surface of the wafer. Thus, secondary electron detecting efficiency is reduced and it causes a reduction in S/N of a secondary electron image, inevitably resulting in a reduction in accuracy of the section observation.

Miniaturization of LSI patterns progresses at a rate of 30% reduction every a few years without stop, and higher resolution is increasingly required in the observation apparatus. Moreover, even if surface distribution of an atomic property X-ray excited by emitting an electron beam is measured by an X-ray detector to carry out elementary analysis (EDX analysis), enlargement of an X-ray generation area due to the electron beam entering into the sample causes surface resolution of analysis to be approximately 1 μm though the electron beam has a diameter equal or less than 0.1 μm, which is insufficient for analysis of the LSI element section having a minute structure.

Fourth, cases where the vertical observation of the section is indispensable include evaluation of workmanship of etching, implantation of grooves or holes, planarization or the like in wafer process. In order to accurately measure a dimension and shape of a processed section, a sample of a chip size including a section to be observed has been determined and observed by a scanning electron microscope for general purpose in the past. However, accompanying with miniaturization progress of devices and enlargement of diameter of the wafer, sometimes failure is resulted since it is considerably difficult to accurately break an element circuit pattern at a position to be observed. However, failure in creating an evaluation sample is not allowed because of poor supply capacity or increased price of the wafer for evaluation.

Fifth, with the technique disclosed in JP-A-5-52721 specification, it is possible to obtain sufficient level of observation and analysis accuracy such as resolution, but the sample has to be manufactured in the conventional apparatus, taken out of the apparatus, and introduced into the separately prepared observation and analysis apparatus, thus there is a problem of requiring hours of time for taking out the minute sample, processing, observation and analysis. Further, in a case where the sample exposed to the air is degraded by oxidation or moisture adsorption, it is difficult to avoid the degradation. Section observation of the semiconductor device has been recently considered to be important as an advantageous inspection technique in manufacturing the semiconductor, and a desirable throughput in that case at present is observation and analysis of more than a few positions per hour, and processing at much higher speed will be desired in the future. Contrary to the desire, the problem of extremely low throughput of the conventional method has not been solved.

In view of the above problems, the present invention has its object to provide a method and apparatus for processing and observing a minute sample, which can vertically observe an inner section of the sample to be observed, and can carry out observation and analysis with high resolution, high accuracy and high throughput without degradation resulting from exposure to the air and without failure.

Another object of the present invention is to provide a minute sample processing apparatus which requires minimum capacity of a vacuum container and a reduced occupying area and has high operability even when the apparatus is intended for a large sample. Still another object of the present invention will be described in embodiments described hereinafter.

In order to attain the above object, there is provided a minute sample processing apparatus, including: a focused ion beam optical system comprising an ion source, a lens for focusing an ion beam and an ion beam scanning deflector; an electron beam optical system comprising an electron source, a lens for focusing an electron beam and an electron beam scanning deflector; a detector for detecting a secondary particle emitted from the sample; and a sample stage on which the sample is placed, wherein the apparatus further comprises a probe for supporting a minute sample cut out by emitting the ion beam to the sample, and a mechanism for operating the probe.

Further, in order to attain another object, there is provided a charged particle beam apparatus, including: a sample stage for placing a sample in a vacuum container; a charged particle source; a irradiation optical system for irradiating a charged particle beam from the charged particle source to the sample; a secondary particle detector for detecting a secondary particle generated from the sample by applying the charged particle beam to the sample; a needle member whose tip is capable of coming into contact with the sample; a probe holder for holding the needle member; an introduction mechanism capable of introducing and extracting the probe holder into and from the vacuum container; and a moving mechanism having a mechanism of slanting the probe holder to a surface of the sample stage.

Structure and technical effects for achieving other objects of the present invention will be described in embodiments described hereinafter.

DETAILED DESCRIPTION OF THE
PREFERRED EMBODIMENTS

A structure and an operation of a minute sample processing and observation apparatus according to the present invention will be described.

(Embodiment 1)

Figure 1:
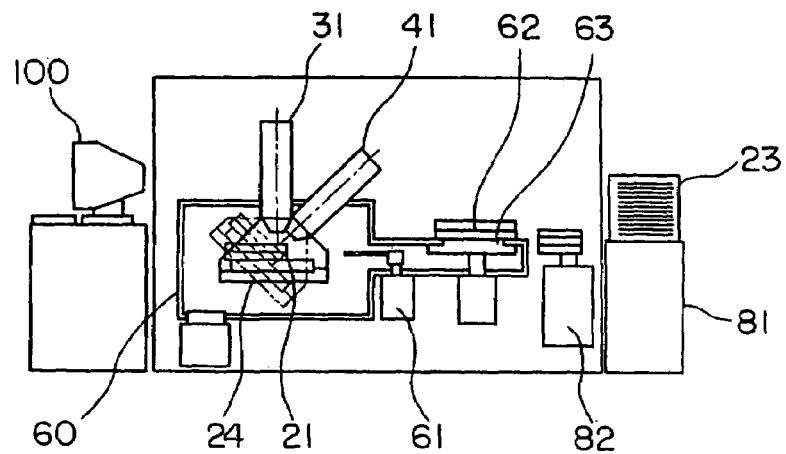
FIG. 1 is a side view of a first embodiment of an apparatus according to the present invention, showing a whole structure thereof.
Figure 2:
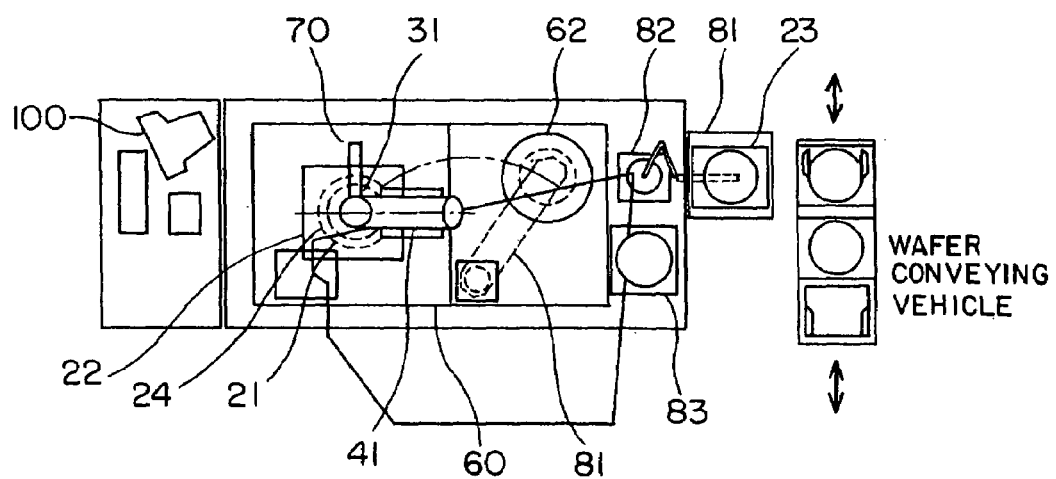
FIG. 2 is a plan view of the first embodiment of the apparatus according to the present invention, showing the whole structure thereof.
Figure 3:
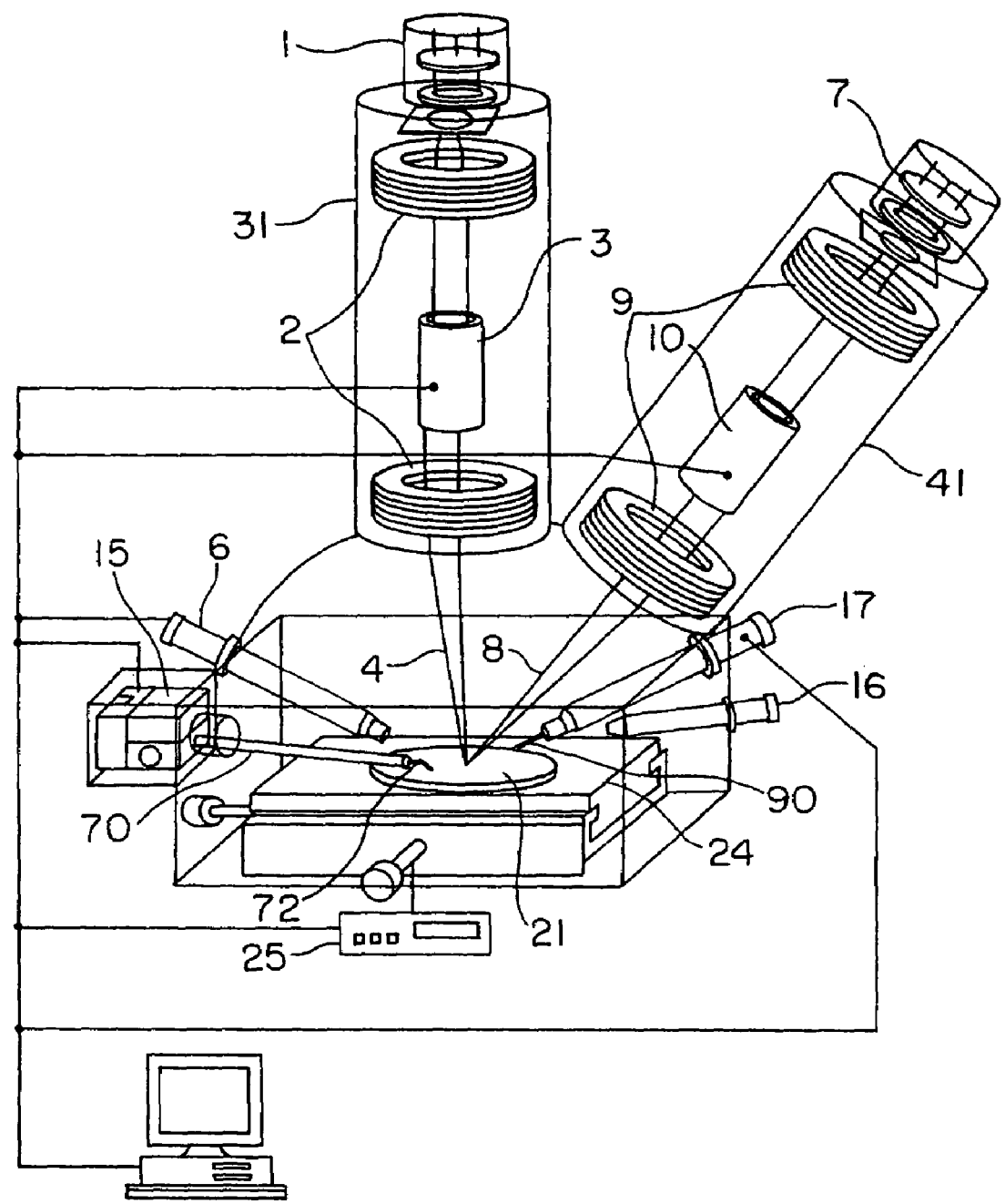
FIG. 3 is a view showing a detailed structure of the first embodiment of the apparatus according to the present invention.

A structure and an operation of a first embodiment of an apparatus of the invention will be described with reference to FIGS. 1, 2 and 3. FIGS. 1 and 2 show a whole structure of the apparatus and FIG. 3 shows structures of a focused ion beam optical system, scanning electron microscope optical system and around a sample stage in detail. Shown in this embodiment is a wafer corresponding apparatus in the minute sample processing and observation apparatus of the present invention. FIG. 3 shows a schematic bird's eye section of FIG. 1, and there are some differences between the figures, though not essential, in orientations or details of apparatuses for convenience in description. In FIG. 1, around a center of an apparatus system are appropriately located a focused ion beam optical system 31 and an electron beam optical system 41 above a vacuum sample chamber 60. A sample stage 24 on which a wafer 21 to be a sample is placed is located inside the vacuum sample chamber 60. Two optical systems 31 and 41 are adjusted in such a manner that their respective central axes intersect at a point on a surface or near the surface of the wafer 21. A mechanism for moving the wafer 21 backward and forward, and right and left with high accuracy is provided in the sample stage 24, and is controlled in such a manner that a designated position on the wafer 21 falls immediately below the focused ion beam optical system 31. The sample stage 24 has functions of rotational, vertical and slanting movements. An exhaust apparatus (not shown) is connected to the vacuum sample chamber 60 and the chamber 60 is controlled so as to have an appropriate pressure. The optical systems 31, 41 also individually comprise respective exhaust systems (not shown) and they are maintained at appropriate pressures. A wafer introducing device 61 and wafer conveying device 62 are provided within the vacuum sample chamber 60. A wafer transferring robot 82 and a cassette introducing device 81 are disposed adjacent to the vacuum sample chamber 60. Provided on the left side of the vacuum sample chamber 60 is an operation controller 100 for controlling the whole apparatus and a series of processing of sample processing, observation and evaluation.

Next, an outline of an operation of introducing the wafer in this embodiment will be described. When a wafer cassette 23 is placed on a table of the cassette introducing device 81 and an operation start command is issued from the operation controller 100, the wafer transferring robot 82 pulls out a wafer to be a sample from a designated slot in the cassette, and an orientation adjustment device 83 shown in FIG. 2 adjusts an orientation of the wafer 21 to a predetermined position. Then, the wafer transferring robot 82 places the wafer 21 on a placement stage 63 when a hatch on an upper portion of the wafer introducing device 61 is opened. When the hatch is closed, a narrow space is formed around the wafer to be a load lock chamber, and after air is exhausted by a vacuum exhaust device (not shown), the placement stage 63 is lowered. Next, the wafer conveying device 62 takes up the wafer 21 on the placement stage 63 and places it on the sample stage 24 at a center of the vacuum sample chamber 60. The sample stage 24 is provided with means for chucking the wafer 21 according to need in order to correct a warp or prevent vibration of the wafer 21. A coordinate value of an observation and analysis position on the wafer 21 is input from the operation controller 100, and the sample stage 24 is moved and stopped when the observation and analysis position of the wafer 21 falls immediately below the focused ion beam optical system 31.

Next, a process of sample processing, observation and evaluation will be described with reference to FIG. 3. In the minute sample processing and observation apparatus of the present invention, the focused ion beam optical system 31 comprises an ion source 1, a lens 2 for focusing an ion beam emitted from the ion source 1, an ion beam scanning deflector 3 or the like, and the electron beam optical system 41 comprises an electron gun 7, electron lens 9 for focusing an electron beam 8 emitted from the electron gun 7, an electron beam scanning deflector 10 or the like. The apparatus is further provided with a secondary particle detector 6 for detecting a secondary particle from the wafer by applying a focused ion beam (FIB) 4 or the electron beam 8 to the wafer 21, the movable sample stage 24 on which the wafer 21 is placed, a sample stage controller 25 for controlling a position of the sample stage for determining a desired sample position, a manipulator controller 15 for moving a tip of a probe 72 to an extracting position of a minute sample, extracting the minute sample and controlling a position or direction optimum for observation and evaluation of a determined position of the minute sample by applying the focused ion beam 4 (FIB) or electron beam 8 to the minute sample, an X-ray detector 16 for detecting an atomic property X-ray excited at the time of applying the electron beam 8, and a deposition gas supplying device 17.

Next, an outline of the process of sample processing, observation and evaluation after introducing the wafer in this embodiment will be described. The sample stage is first lowered and the probe 72 is horizontally (in X and Y directions) moved relative to the sample stage 24 with the tip of the probe 72 separated from the wafer 21, and the tip of the probe 72 is set in a scanning area of the FIB 4. The manipulator controller 15 which is a mechanism for operating the probe stores a positional coordinate and then evacuates the probe 72.

Figure 4:
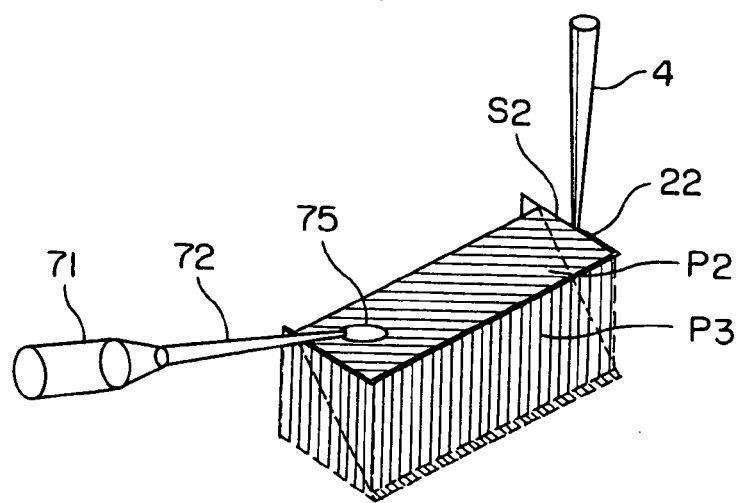
FIG. 4 is a view showing an example of a minute sample processing method of the present invention.

The focused ion beam optical system 31 applies the FIB 4 to the wafer 21 to form a rectangular U-shaped groove across an observation and analysis position p2 as shown in FIG. 4. A processing area has a length of about 5 μm, width of about 1 μm and depth of about 3 μm, and is connected to the wafer 21 at its one side surface. Then, the sample stage 24 is inclined, and an inclined surface of a triangular prism is formed by the FIB 4. In this condition, however, the minute sample 22 is connected with the wafer 21 by a support portion S2.

Then, the inclination of the sample stage 24 is returned, and thereafter, the probe 72 at the tip of the manipulator 70 is brought into contact with an end portion of the minute sample 22. Then, the deposition gas is deposited on a contact point 75 by application of the FIB 4, and the probe 72 is joined to and made integral with the minute sample 22. Further, the support portion S2 is cut by the FIB 4 to cut out the minute sample 22. The minute sample 22 is brought into a condition of being supported by the probe 72, and ready is completed that a surface and an inner section of the minute sample 22 for the purpose of observation and analysis is taken out as an observation and analysis surface p3.

Figure 5:
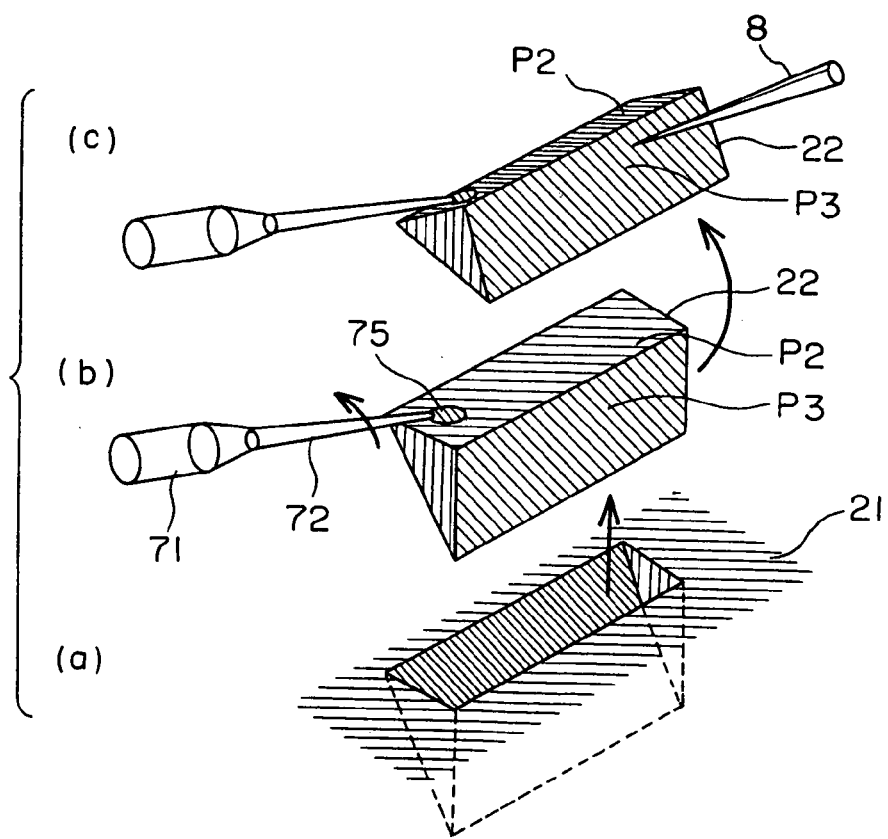
FIG. 5 is views showing an example of a minute sample observation method of the present invention.

Next, as shown in FIG. 5(b), the manipulator 70 is operated to lift the minute sample 22 up to a level apart from the surface of the wafer 21. If necessary, the observation section p3 of the minute sample 22 may be additionally processed to a desired shape by appropriately adjusting the application angle of the FIB 4 with rotating operation of the manipulator. As an example of the additional processing, there is a finishing processing for forming an observation section p2 slantingly formed by tapering of the beam of the FIB 4 to be a real vertical section. In section processing/observation having been performed hitherto, an observation surface has to be a side wall of a hole dug by the FIB, while in the apparatus of this embodiment, the sample can be additionally processed after being lifted, with the observation surface thereof appropriately moved. Therefore, it becomes possible to form a desired section appropriately.

Then, the minute sample 22 is rotated, and the manipulator 70 is moved in such a manner that the electron beam 8 of the electron beam optical system 41 substantially vertically enters into the observation section p3 to control attitude of the minute sample 22, and then stopped. Thus, even in case of observing a section of the sample, detection efficiency of a secondary electron by the secondary particle detector 6 is increased as much as in the case of observing an outermost surface of the wafer. Observation condition of the observation and analysis surface p3 of the minute sample 22 is greatly improved. A reduction in resolution which has been a problem in the conventional method can be avoided. The angles of the observation and analysis surfaces p2, p3 can be adjusted to desirable angles, and therefore, it becomes possible to perform more exact observation and analysis. With this, direction of observation of the inner section of an object sample can be freely selected. Consequently, there can be provided a minute sample processing and observation apparatus which permits observing a shape and dimension of etching or planarization, an implanting condition, coating thickness or the like with high resolution by substantially vertically observing the section, and achieving measurement and evaluation with high accuracy.

In this embodiment, the resolution can be improved by transferring a minute sample by movement of the manipulator 70 immediately below the electron beam optical system 41 to reduce a working distance. In an apparatus, like this embodiment, in which an ion beam optical system and an electron beam optical system are disposed in one vacuum container, a space in the vacuum container is limited, and it is difficult to bring a large sample close to the electron beam optical system. However, by positioning a cut-out minute sample below the electron beam optical system as is in this embodiment, such a problem can be solved.

Further, the minute sample 22 is observed and analyzed while being placed in the sample chamber of a vacuum atmosphere without taken out of the apparatus, so that observation and analysis of the inner section of the sample to be observed and analyzed can be achieved with high resolution, high accuracy and an optimum angle without contamination or deposition of foreign materials resulting from exposure to the outside atmosphere. In addition, observation and analysis can be achieved with high throughput of processing more than a few positions per hour. This method also allows observation to be carried out simply by lifting and appropriately positioning the minute sample, which permits facilitating operation and reduction in operation time.

In this embodiment, the section of the semiconductor sample cut by FIB application is moved substantially perpendicularly to the optical axis of the scanning electron microscope to be observed. Thus, an extremely meritorious effect is exerted in such a case of observing a thin film layer formed in the semiconductor sample. For example, wiring formed in the semiconductor wafer has been often formed from copper or the like these days. Metal such as copper tends to be diffused in the semiconductor wafer to degrade the property of the semiconductor, so that it is necessary to form a barrier metal around the wiring to prevent diffusion. The barrier metal is an extremely thin film with a thickness on the order of 0.01 μm to 0.02 μm when the wiring has a thickness of 0.1 μm to 0.2 μm, and is formed from metal such as tantalum. In an inspection process of the semiconductor wafer, whether a barrier metal is formed appropriately or not is an important inspection item.

When the electron beam is slantingly emitted with respect to the observation section as in the conventional section processing and observation, a distance that the electron beam interferes in the sample is increased to reduce the resolution of the scanning electron microscope and to sometimes make it difficult to observe the barrier metal. Further, since the barrier metal is the thin film as described above, the electron beam entering into the barrier metal sometimes interferes adjacent other material areas. In such a case, there is a possibility of detecting information on other materials from a position where materials constituting the barrier metal only should exist. Thus, information on the copper of the adjacent wiring is detected regardless of the barrier metal being appropriately formed, which leads to a possibility of obtaining an inspection result that function as the barrier metal is not effected. This presents a problem especially in an EDX analysis for analyzing composition of a sample by detecting a property X-ray specific to material which is resulted from the electron beam application.

The metal which forms the wiring or barrier metal is sometimes corroded or oxidized at its surface when made in contact with the air, thus making it difficult to observe the section.

In this embodiment, for solving the above two problems together, observation by the scanning electron microscope capable of non-destructive observation with high resolution can be achieved in a vacuum atmosphere where the sample is cut out, and the electron beam application perpendicularly to the sample section is permitted. With this structure, it become possible to carry out section processing and observation of the semiconductor element which is becoming increasingly more minute with high resolution and accuracy.

Further, also in a case an additional processing is effected after observation by the scanning electron microscope, the minute sample can be positioned below the optical axis of the FIB without being exposed to the air. Therefore, there is no possibility that a position to be additionally processed is hidden by the oxide film and alignment of processing positions becomes impossible.

Further, in this embodiment, the minute sample 22 having the observation and analysis surface p3 can be inclined or moved in various ways by the manipulator 70. Thus, it becomes possible, for example, to provide a hole in the observation section p2 and to also confirm three-dimensional fault forming condition in the sample.

In the example shown in FIG. 3, the manipulator 70 and the electron beam optical system 41 are provided opposite to each other with respect to the FIB 4. However, in order to reduce the number of operation of the manipulator 70 or the like to minimize processing/observation time, it is preferable that a relative angle between the manipulator 70 and the electron beam optical system 41 is set close to 90° in a surface perpendicular to the application direction of the FIB 4. The reason is that by setting so, it is sufficient that the manipulator 70 simply carries out an operation of lifting the minute sample 22 from the wafer 21, operation of rotating the probe 72 in such a manner that the observation section p2 is perpendicular to the electron beam 8, and other fine adjustment operations.

Used in the above description is an example of lifting the minute sample 22 from the wafer 21 by the manipulator 70, but not limited to this. The wafer 21 may be lowered to thereby consequently lift the minute sample 22. In this case, the sample stage 24 is provided with a Z-axis moving mechanism for moving the wafer 21 in a Z direction (an optical axis direction of the FIB 4). With this structure, it becomes possible to perform cutting out and lifting of the minute sample 22 in a condition where the optical axis of the electron beam optical system 41 is located in the portion of the wafer 21 to be the minute sample 22. In this case, the process from cutting out the minute sample 22 by the FIB 4 to observing the observation section p2 can occur with confirmation by the electron microscope without frequent changes of electron beam application positions during the process.

By the electron beam optical system 41, an electron microscope image of the surface of the wafer 21 slantingly viewed can be obtained. A section to be processed or processing arrival position by the FIB 4 is superposed on the electron microscope image to be model displayed, then the section processing condition by the FIB 4 can be easily confirmed. In order to display the section to be processed in a superposed manner on the electron microscope image, animation showing a portion to be a section is displayed on the electron microscope image in the superposed manner based on a processing depth to be set and a dimension in the electron microscope image calculated from magnification.

If the processing depth is calculated in real time based on current and acceleration voltage of the FIB, material of the sample and the like, and an animation showing the present processing depth are displayed in an interposed manner on the electron microscope image, it becomes easy to confirm progress of the processing. The electron beam optical system 41 of this embodiment is disposed in a bird's eye position with respect to the wafer 21, and the electron microscope image becomes a bird's eye image. Therefore, by displaying also the above-described animation into three-dimensional display together with the electron microscope image, it is possible to confirm the processing condition more clearly.

Further, this embodiment has a function of setting a position of the section processing on a scanning ion microscope image (SIM image) formed on the basis of the secondary electron obtained by scanning the wafer 21 with the FIB. However, it is possible to provide also a sequence where other setting and operation of the apparatus (driving of the sample stage and determination of the processing position by the ion beam) are automatically carried out based on inputs of the section position and the processing depth. In this case, a portion to be an upside of the observation section p3 is first designated on the SIM image, and the processing depth (a dimension in the depth direction of the observation section p3) is set. Based on these two settings, the forming angle of the inclined portion of the minute sample 22 and the observation and analysis surface p3 are automatically determined, and the subsequent processing is automatically carried out by the settings. It is also possible to provide a sequence where the subsequent processing is automatically carried out by setting the observation and analysis surface p3 (rectangular area) on the SIM image and setting the processing depth.

In this embodiment, after the minute sample 22 is lifted, the probe 72 is operated so that the observation section p3 is appropriately positioned with respect to the electron beam 8. In FIG. 4, for example, when simply rotating the probe 72, the minute sample 22 is rotated around an attachment point to the probe 72. Therefore, the observation section p3 includes components of not only a rotation around a longitudinal axis of the minute sample 22 but also a rotation around an axis in the application direction of the FIB 4. Imparting a mechanism for removing the rotational components to the manipulator or manipulator controller, and operating the manipulator in timing compliant with the rotation of the probe 72 or timing different from the rotational operation allow the observation section p3 to be accurately positioned in a surface perpendicular to the optical axis of the electron beam 8.

The same effect can be obtained by disposing the probe 72 to have an angle slightly larger than 90° to the electron beam optical system 41 in the surface perpendicular to the optical axis of the FIB 4. In this case, the effect is achieved by disposing the probe 72 to a rotational component around the axis in the application direction of the focused ion beam plus 90° with respect to the electron beam optical system 41.

Including the rotational component around the axis in the application direction of the FIB 4 is resulted from the rotation axis of the probe 72 being inclined with respect to the observation and analysis surface p2 and the observation section p3. That is, the above problem can be solved by forming the probe 72 such that the rotation axis becomes parallel to the observation and analysis surface p2 and observation section p3. Therefore, in a case of the apparatus having a mirror structure as shown in FIG. 3, the rotation axis of the probe 72 is preferably formed in parallel with the surface of the wafer 21 (perpendicular to the optical axis of the FIB 4). By curve the tip of the probe 72, even a probe having the rotation axis parallel to the surface of the wafer 21 can support the minute sample 22. Further, it is preferable to form the rotation axis of the probe 72 so as to be perpendicular to the electron beam optical system 41 so that the sample can be moved below the optical axis of the electron beam 8 by rotation and parallel movement of the probe. Specific examples of the structure of the probe will be further described in detail in a description on a subsequent embodiment.

If a mechanism to transfer a driving power from the manipulator controller 15 to a probe having a rotation axis with a different height from a probe holder 71 and parallel to the wafer 21 is provided, alignment of the observation section p3 with the electron beam 8 can be carried out without moving the minute sample 22 on a large scale.

Figure 18:
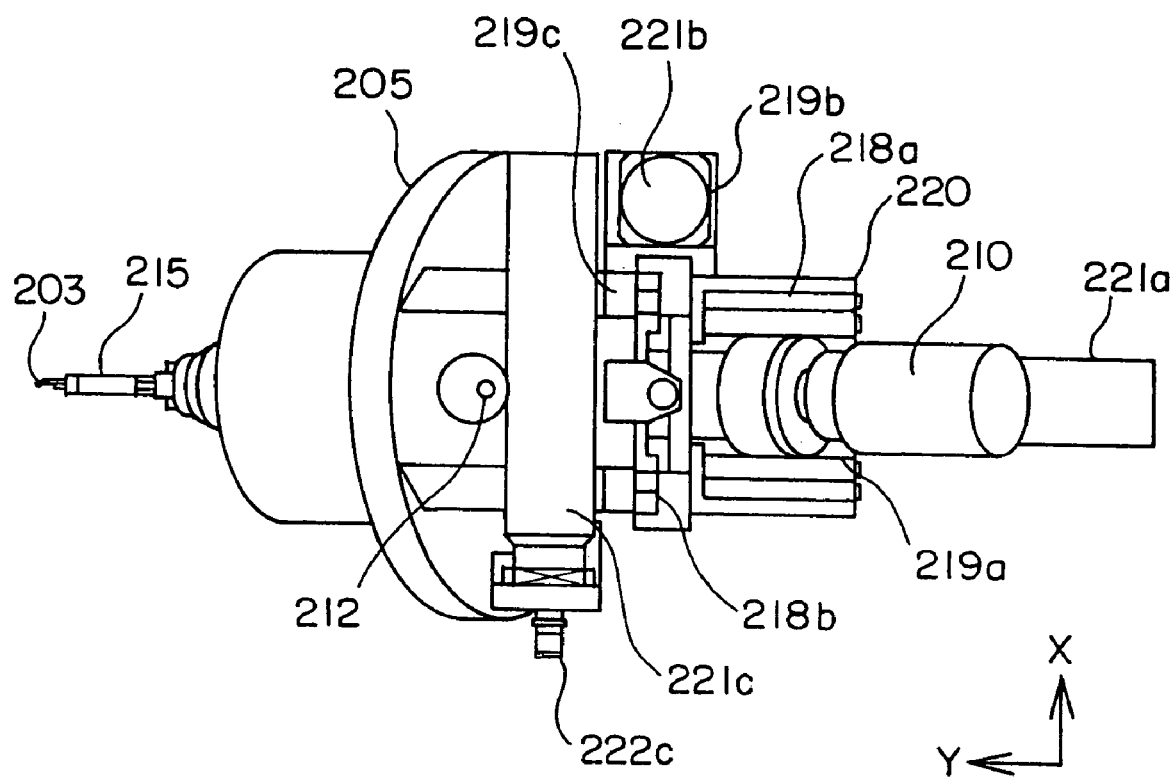
FIG. 18 is a plan view of the probe moving mechanism for the sample creating apparatus of the fifth embodiment of the present invention.

The minute sample 22 in a suspended condition by the probe 72 is susceptible to vibration, thus in observation and analysis with high magnification and in a locating environment of much vibration, the minute sample 22 may be grounded on a safe position on the wafer 21 or grounded on a minute sample port provided on a space around the wafer on the sample stage to thereby substantially restrain the vibration of the minute sample, permitting superior observation and analysis. FIG. 18 shows an example thereof such that earthquake resistance is improved by grounding the cut-out minute sample 22 on the wafer 21. In adopting such a method, it is preferable to make a sequence in advance such that the grounding position of the minute sample matches the optical axis of the electron beam 8.

In creating the minute sample 22 shown in FIG. 4, the minute sample 22 is processed into pentahedron. This achieves creating of the minute sample especially with reduced waste in processing and in a reduced period of time for separation of the minute sample. It is needless to say that the same effect of the present invention can be obtained by forming the minute sample 22 into tetrahedron (not shown) or a shape close to tetrahedron which can minimize processing time because of the least processing surface.

In the EDX analysis in which the electron beam 8 is scanned on the minute sample 22, elementary analysis accuracy is improved by forming the minute sample 22 thinner in the electron beam application direction than an entry distance of about 1 μm by the electron beam application. The EDX analysis is carried out using a detector of an X-ray generated from the minute sample resulting from the electron beam application. Forming the minute sample to be a thinner film permits avoiding enlargement of an X-ray generation area resulting from entry of a charged particle beam, thus enabling the elementary analysis with high resolution.

By applying the analysis thus far described to the semiconductor wafer with or without pattern, the analysis can be used in an inspection of a semiconductor manufacturing process to contribute to improvement of manufacturing yield by early detection of failure and quality control in a short period of time.

(Embodiment 2)

Figure 6:
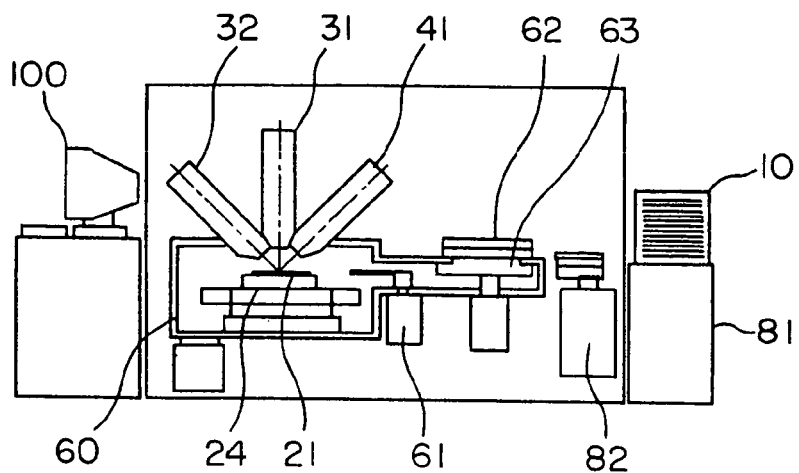
FIG. 6 is a side view of a second embodiment of the apparatus according to the present invention, showing a whole structure thereof.
Figure 7:
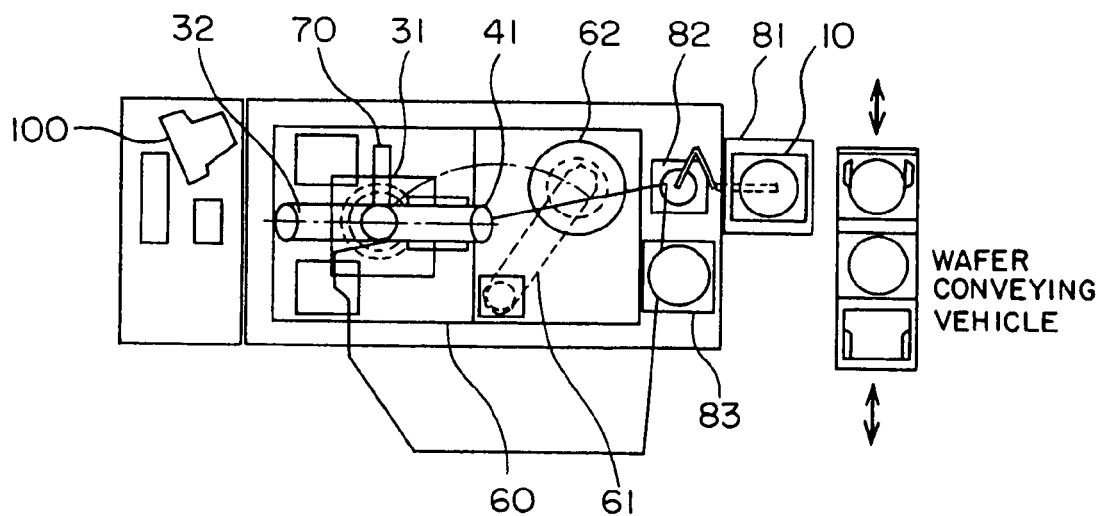
FIG. 7 is a plan view of the second embodiment of the apparatus according to the present invention, showing the whole structure thereof.

A structure and an operation of a minute sample processing and observation apparatus according to a second embodiment of the present invention will be described with reference to FIGS. 6 and 7. FIG. 7 is a plan view of FIG. 6, and there are some differences between the figures in orientations or details of apparatuses for convenience in description but they are not essential differences. In this apparatus, a focused ion beam optical system 31 is vertically disposed and a second focused ion beam optical system 32 is located at an angle of approximately 40° at the upper part of a vacuum sample chamber 60 disposed in the central part of the apparatus system. An electron beam optical system 41 is slantingly located at an angle of approximately 45°. Three optical systems 31, 32, 41 are adjusted in such a manner that their respective central axes intersect at a point around a surface of a wafer 21. Similarly to the apparatus of the first embodiment, inside the vacuum sample chamber 60 is located a sample stage 24 on which the wafer 21 to be a sample is placed. The sample stage 24 in this embodiment has functions of horizontal (X-Y), rotational and vertical movements, but a slanting function is not necessarily required.

Next, a sample creating operation by this apparatus will be described with reference to FIG. 4. An FIB 4 is applied from the focused ion beam optical system 31 to the wafer 21 to form a rectangular U-shaped groove across an observation and analysis position p2 as shown in FIG. 4. This is identical to the first embodiment. Then, an inclined surface of a triangular prism is formed by processing with the FIB 4 from another focused ion beam optical system 32. In this condition, however, the minute sample 22 and wafer 21 are connected with each other by a support portion. Then, a minute sample is cut out using the FIB 4 from the focused ion beam optical system 31 similarly to the first embodiment. That is, a probe 72 at a tip of a probe holder 71 of a manipulator 70 is brought into contact with an end portion of a minute sample 22, and then deposition gas is deposited on a contact point 75 by application of the FIB 4, where the probe 72 is joined to and made integral with the minute sample 22, and the support portion is cut by the FIB 4 to cut out the minute sample 22. Subsequent steps of observation and analysis of the minute sample 22 are identical to the first embodiment.

As described above, also in this embodiment, high speed observation and analysis with high resolution can be achieved similarly to the first embodiment. In this embodiment, slanting of the sample stage can be eliminated especially by using two focused ion beam optical systems. Omitting the slanting mechanism of the sample stage can improve positioning accuracy of the sample stage more than a few to ten times. In a manufacturing site of LSI devices, it has come into practice in recent years that various wafer inspection and evaluation apparatus carry out a foreign material inspection and defect inspection, that a property and coordinate data of a wrong portion on the wafer are recorded, and that subsequent apparatus for a further detail inspection receives the coordinate data to determine a designated coordinate position and to carry out observation and analysis. High positioning accuracy permits automation of determining the observation position of the wafer 21 and simplification of its algorithm. This can substantially reduce required time, which permits obtaining high throughput. Further, the sample stage having no slanting mechanism is compact and lightweight and can easily obtain high rigidity to increase reliability, thus permitting superior observation and analysis and miniaturization or a reduction in cost of the apparatus.

Imparting a swinging function to the focused ion beam optical system 31 to be appropriately moved between the vertical and inclined positions permits processing identical to the second embodiment without slanting the sample stage 24, and thus the effect of the present invention can be obtained.

(Embodiment 3)

Figure 8:
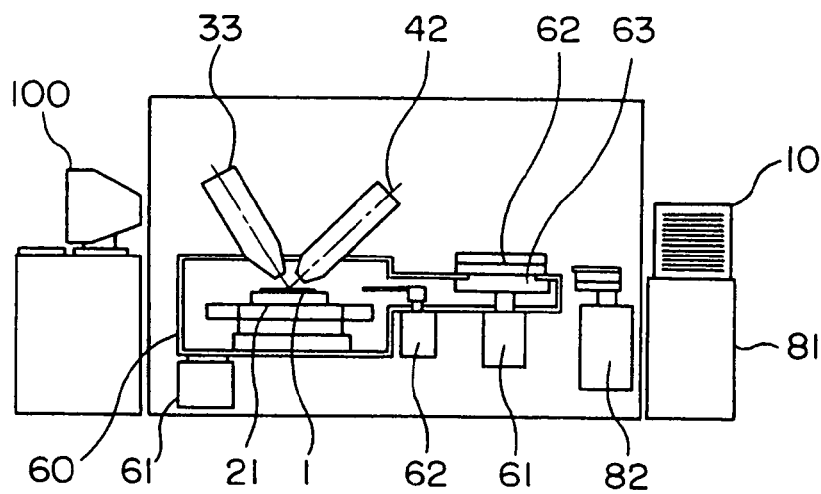
FIG. 8 is a side view of a third embodiment of the apparatus according to the present invention, showing a whole structure thereof.
Figure 9:
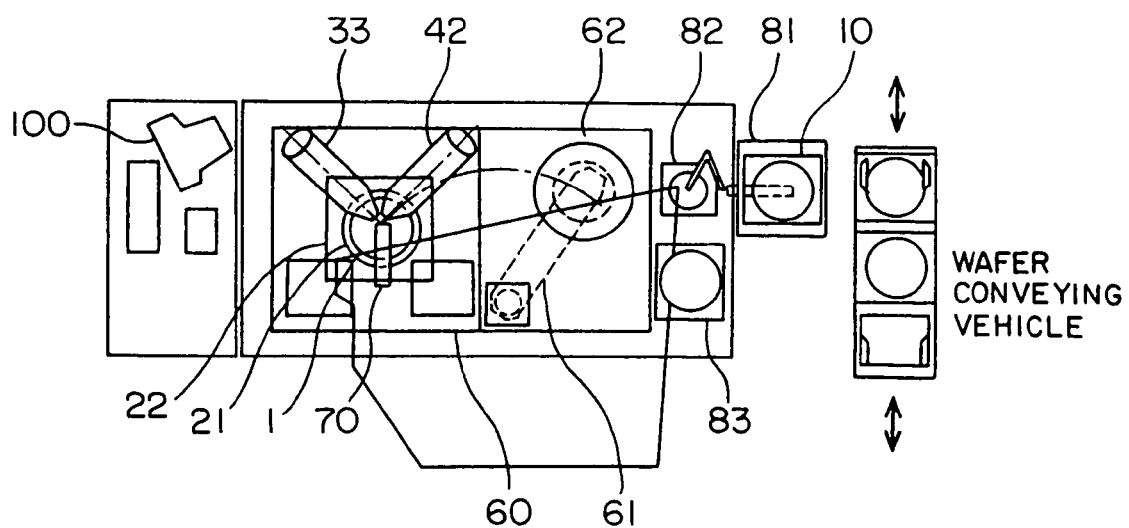
FIG. 9 is a plan view of the third embodiment of the apparatus according to the present invention, showing the whole structure thereof.

A structure and an operation of a minute sample processing and observation apparatus according to a third embodiment of the present invention will be described with reference to FIGS. 8 and 9. FIG. 9 is a plan view of FIG. 8, and there are some differences between the figures in orientations or details of apparatuses for convenience in description but they are not essential difference. In the apparatus of this embodiment, a focused ion beam optical system 33 is slantingly located at an angle of approximately 45° at an upper portion of a vacuum sample chamber 60 disposed at the central part of the apparatus system. An electron beam optical system 42 is also slantingly located at an angle of approximately 45°. Two optical systems 33, 42 are adjusted in such a manner that their respective central axes intersect at a point around a surface of a wafer 21. Similarly to the apparatus of the first embodiment, inside the vacuum sample chamber 60 is located a sample stage 24. Further, similarly to the second embodiment, the sample stage 24 has no slanting function.

Next, processes of sample processing, observation and evaluation after introducing the wafer will be described with reference to FIG. 19 also. The sample stage is first lowered to move a probe 72 horizontally (in X and Y directions) relative to the sample stage 24 with the tip of the probe 72 separated from the wafer 21, and the tip of the probe 72 is set in a scanning area of the FIB 4. The manipulator controller 15 stores a positional coordinate and then evacuates the probe 72.

The sample stage is oriented in such a manner that an intersection line of a vertical plane containing an optical axis of a focused ion beam optical system 33 and a top surface of the wafer is superposed on an observation section of a sample to be formed. Then, an FIB 4 is applied to the wafer 21 for scanning to form a vertical section C1 having a length and depth required for the observation. Then, an inclined cut section C2 which intersects a formed section is formed. When forming the inclined cut section C2, the sample stage is rotated around a horizontal axis up to a position where an inclination angle of an inclined surface is obtained to determine the orientation. Next, an inclined groove is formed by the FIB 4 in parallel with a vertical cut line. Further, an end C3 is cut orthogonal to the groove. A processing area has a length of about 5 µm, width of about 1 µm and depth of about 3 µm, and is connected to the wafer 21 in a cantilevered condition of a length of about 5 µm. Then, the probe 72 at the tip of a manipulator 70 is brought into contact with an end portion of a minute sample 22, and then deposition gas is deposited on a contact point 75 by application of the FIB 4, where the probe 72 is joined to and made integral with the minute sample 22. Then, the other end C4 supporting the minute sample is cut by the FIB 4 to cut out the minute sample 22. The minute sample 22 is brought into a condition of being supported by the probe 72, and ready to be taken out with a surface and an inner section for the purpose of observation and analysis as an observation and analysis surface p3 is completed. Processing thereafter is substantially identical to the first embodiment except that an orientation of the sample stage 24 is also required to be appropriately adjusted when setting the optimum orientation of the minute sample for processing and observation by the focused ion beam optical system or observation by electron beam optical system, and thus description thereof will be omitted.

As described above, also in this embodiment, high speed observation and analysis with high resolution can be achieved similarly to the first embodiment. This embodiment has a feature that one focused ion beam optical system is inclined with respect to the sample stage to thereby cut out and extract the minute sample from the wafer without imparting a slanting function to the sample stage. Generally, a large number of devices are required to be mounted around the optical system, causing lack of spaces, and a large total mass of the devices makes difficult design of a mounting substrate including ensuring rigidity. Maintenance thereof is also a matter of concern. This embodiment eliminates the need for a slanting mechanism of the sample stage, and requires only one focused ion beam optical system, which can provide a simple, compact and lightweight structure and reduced cost.

(Embodiment 4)

Figure 10:
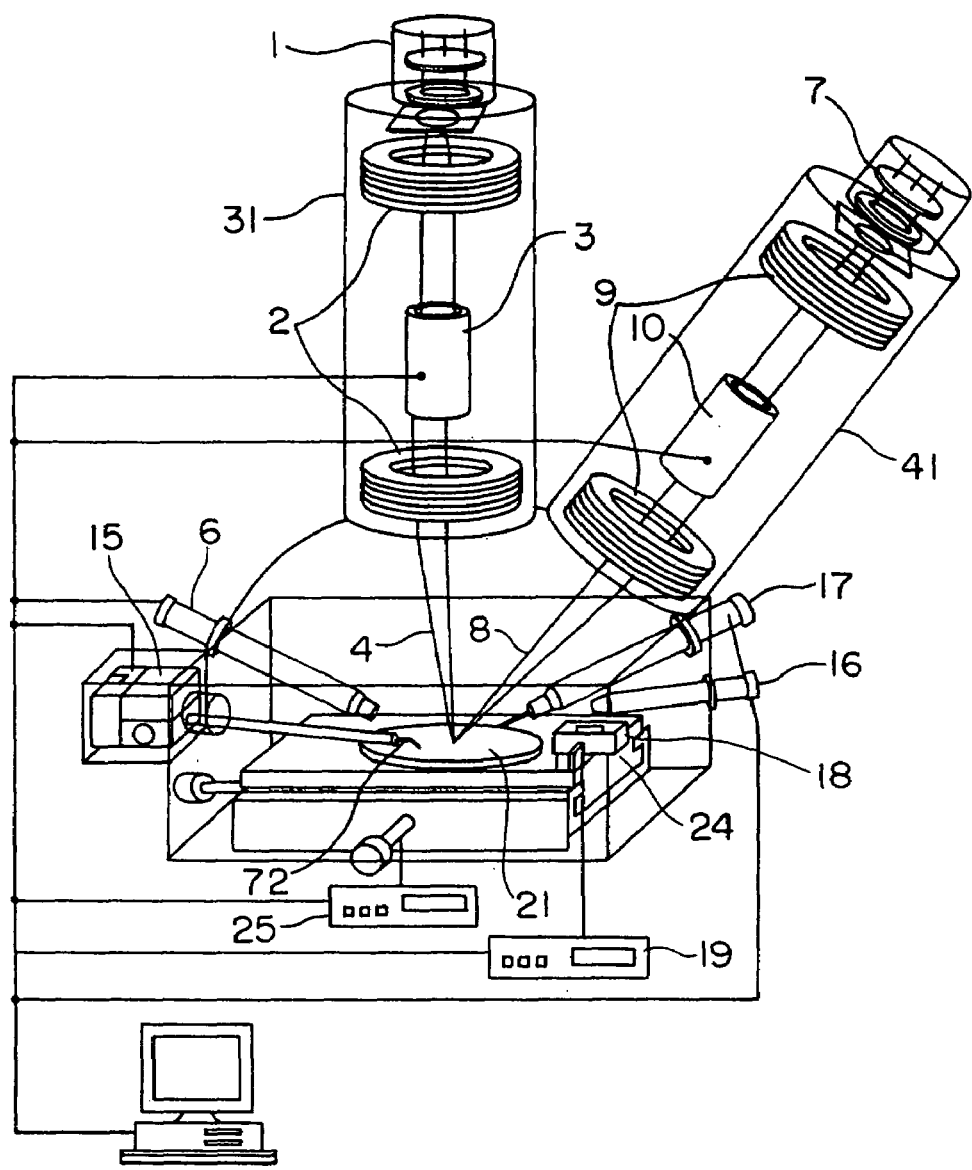
FIG. 10 is a view showing a detailed structure of the fourth embodiment of the apparatus according to the present invention.

An outline of structure of a minute sample processing and observation apparatus according to a fourth embodiment of the present invention will be described with reference to FIG. 10. In this embodiment, a second sample stage 18 and second sample stage controller 19 for controlling an angle, a height and the like of the second sample stage are added to a basic structure of the minute sample processing and observation apparatus shown in FIG. 3. The process from applying an ion beam from the focused ion beam optical system 31 to a wafer to extracting a minute sample from the wafer is identical to the first embodiment. In this embodiment, the extracted minute sample is fixed to the second sample stage for observation and analysis instead of observation and analysis in the supported condition by the manipulator.

Figure 11:
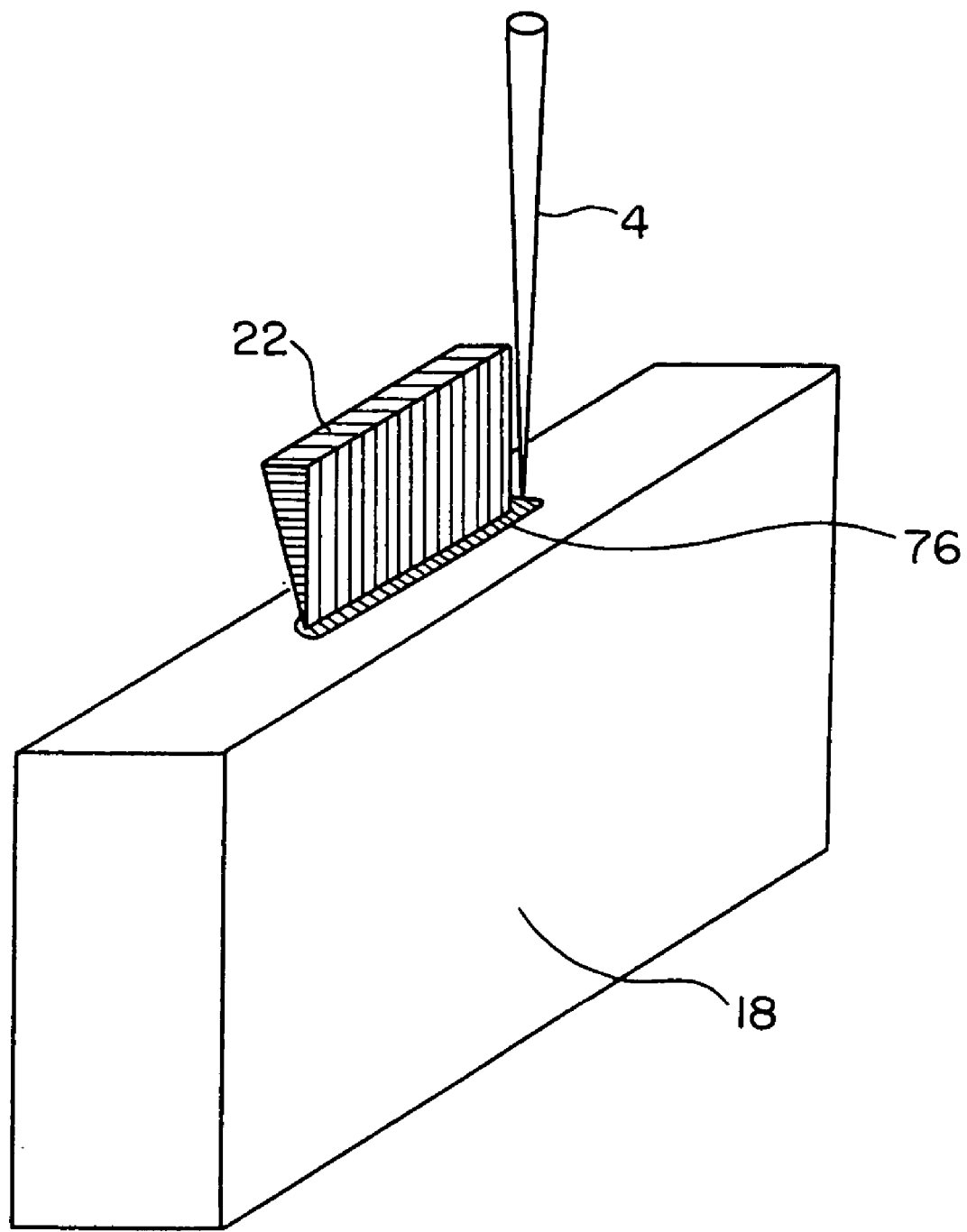
FIG. 11 is a view showing an example of a minute sample fixed to a second sample stage in the fourth embodiment of the present invention.

FIG. 11 shows a condition of the minute sample 22 fixed to the second sample stage 18. A member with a flattened surface is used for a minute sample fixed portion of the second sample stage 18 in this embodiment, but flatness does not matter. A bottom surface of the minute sample is brought into contact with the second sample stage 18, and deposition gas is deposited on a contact point between the second sample stage 18 and minute sample 22 with the FIB 4 to fix the minute sample 22 to the second sample stage 18 with an assist deposition film 76. In order to prevent inconvenience of attachment of foreign materials to the surface of the observation section or destruction of the surface of the observation section when creating the minute sample 22 or depositing the deposition gas, an application angle of the FIB 4 may be appropriately set in parallel to the observation section of the minute sample by operating the second sample stage to create a desired observation section by applying the FIB 4.

Figure 12:
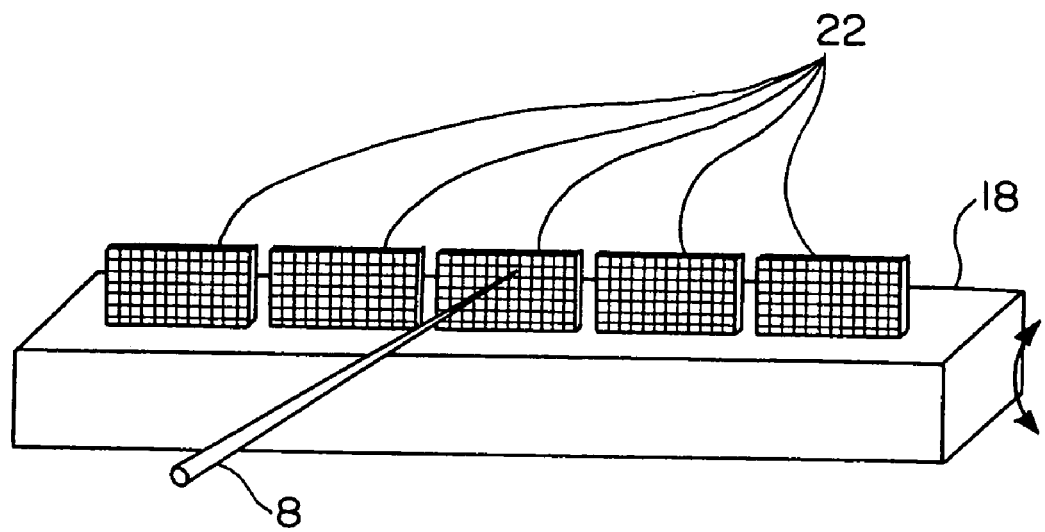
FIG. 12 is a view showing details of essential portions of the fourth embodiment of the present invention.

By locating the second sample stage shown in FIG. 12, a plurality of minute samples can be collectively handled. By repeating operation of extracting the minute sample 22 from the wafer 21 to fix it to an appropriate position on the second sample stage 18 beside the first sample stage, section observation and elementary analysis of the plurality of samples can be carried out with the wafer 21 fixed to the sample stage 24, and distribution of a section structure throughout the wafer 21 can be efficiently examined.

Figure 13:
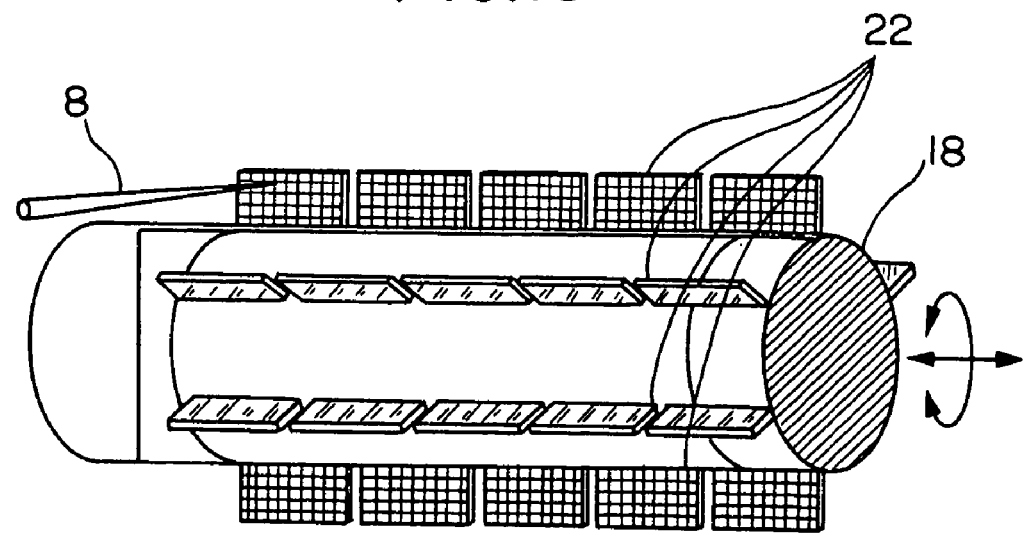
FIG. 13 is a view showing details of essential portions of the fourth embodiment of the present invention.
Figure 14:
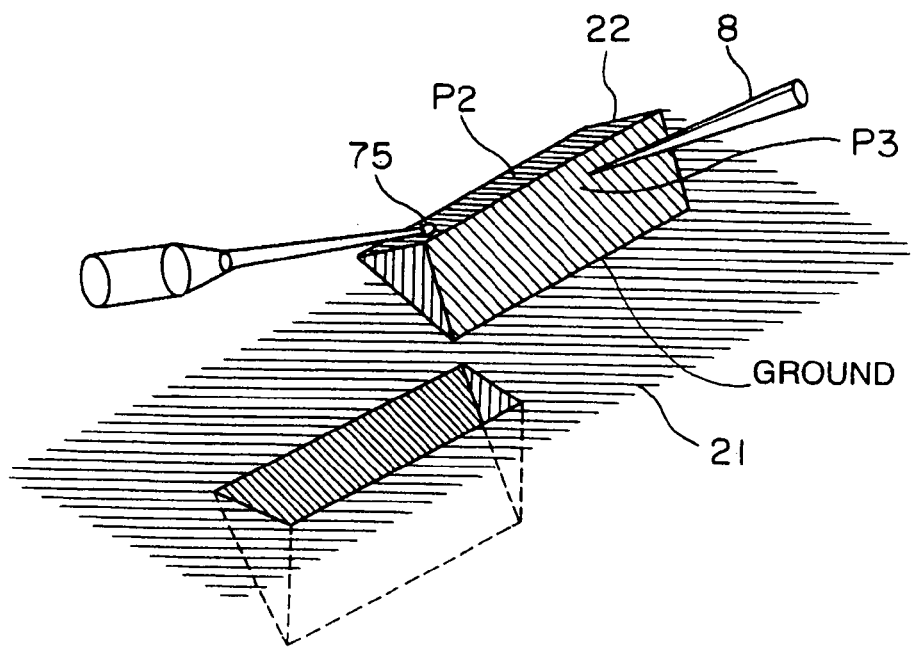
FIG. 14 is a view showing an example of a minute sample observation method.
Figure 15:
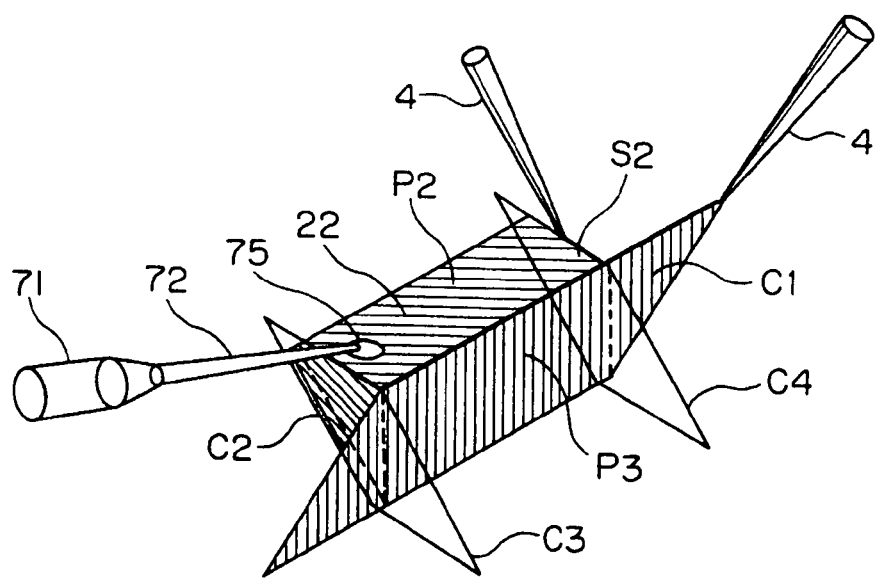
FIG. 15 is a view showing an example of a minute sample processing method.

In FIG. 12, when fixing the plurality of minute samples in a line to the second sample stage 18 and carrying out observation and analysis in a condition where both of a stopping orientation of the sample stage 24 and an angle of the second sample stage 18 are adjusted so as to locate the minute sample 22 at an appropriate angle to the electron beam 8, the plurality of minute samples can be observed and analyzed successively or repeatedly with compared to one another, thereby permitting detailed and efficient examinations of the section structure and elementary distribution throughout the wafer 21. The second sample stage 18 shown in FIG. 13 is a rotatable column sample stage such that a minute sample group can be arranged on its outer peripheral surface, and a larger number of minute samples can be handled at a time than in the case of FIG. 12.

By detaching the minute samples 22 to be recovered in a designated position in a sample recovery tray and providing identification means for the minute samples, the minute samples 22 can be taken out again for observation and analysis when a detailed evaluation is required afterward.

As described above, also in this embodiment, secondary electron detecting efficiency can be obtained as high as in the case of observing the wafer surface, an angle for observation and analysis can be adjusted to a desirable angle including vertical observation, observation can be carried out with placed in a sample chamber of a vacuum atmosphere, and the like, therefore, observation condition of the minute sample 22 is greatly improved to permit avoiding a reduction in resolution which has been a conventional problem and carrying out optimum, exact observation and analysis promptly with high speed and high efficiency. As a result, superior observation and analysis can be carried out with high throughput. By separating the minute sample from the manipulator to be fixed to the second sample stage, vibration isolating mechanism of the sample stage which holds the introduced sample and vibration isolating mechanism of the second sample stage to which the minute sample is fixed can be shared.

(Embodiment 5)

Figure 16:
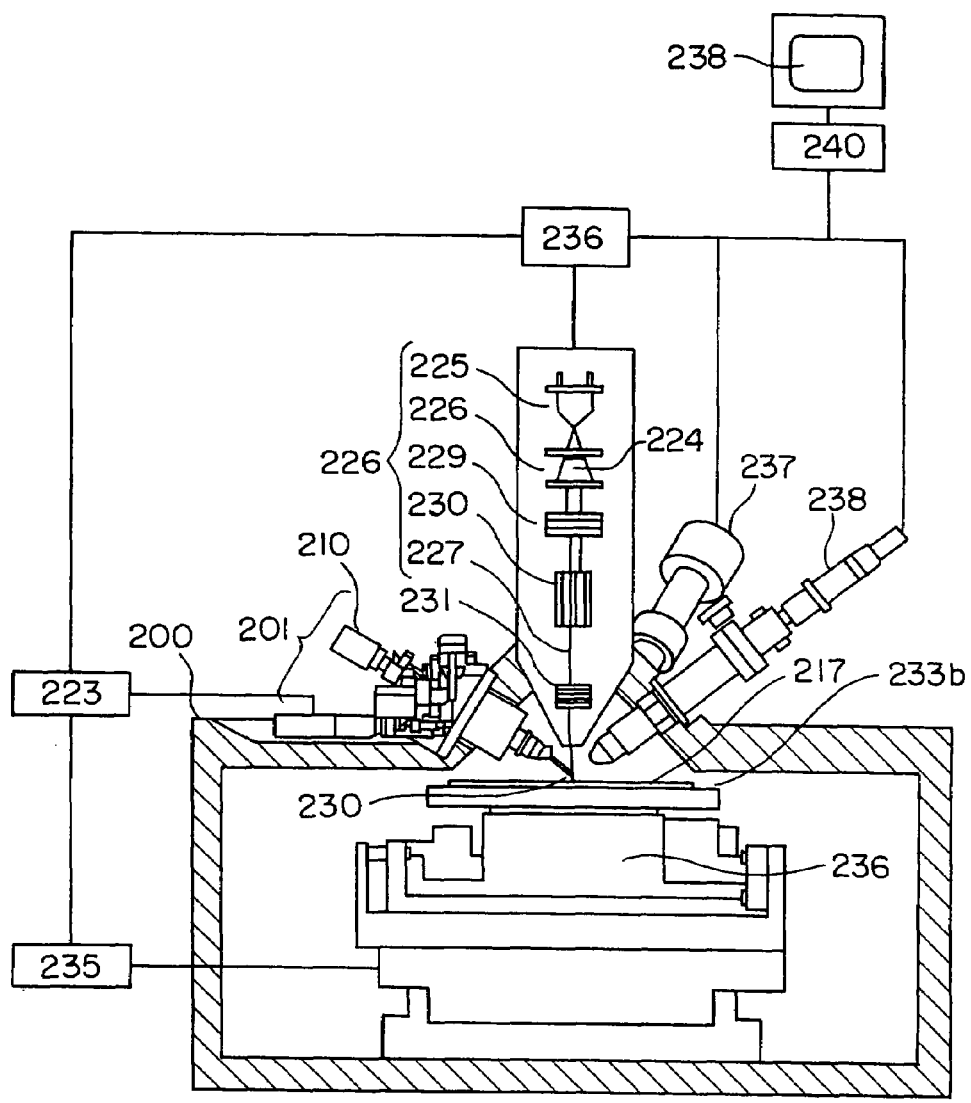
FIG. 16 is a sectional view of a sample creating apparatus of a fifth embodiment of the present invention.

Details of the probe for lifting the minute sample from the wafer, which has been described in the former embodiments and a driving mechanism for driving the probe will be described below. FIG. 16 is an explanatory view of the embodiment. In this embodiment, an example where the probe for lifting the minute sample from the wafer and the like and a holder for holding the probe are detachably mounted to a sample chamber (vacuum container) will be described.

An optical system 226 comprising an ion source 225, beam limiting aperture 228, focusing lens 229, deflector 230 and objective lens 231 are basically the same as in FIG. 3, and an FIB 227 is adjusted which is applied along an optical axis 224. Further, the apparatus shown in FIG. 16 is provided with a sample holder 233a for holding a wafer 217 and a stage 234 for moving the sample holder in X-Y directions.

The apparatus is further provided with a secondary electron detector 237 for detecting a secondary electron discharged from the sample resulting from application of the FIB 227, a deposition gas source 238 for blasting a deposition gas concurrently with application of the ion beam and a vacuum container 206 for maintaining high vacuum in the sample chamber. An output of the secondary electron detector 237 is amplified by an amplifier (not shown) and then stored in an image memory (not shown) and displayed on an image display apparatus 238. A central processing unit 240 controls various components of the apparatus shown in FIG. 16 via an FIB controller 236, a probe position controller 223, and stage position controller 235.

Figure 17:
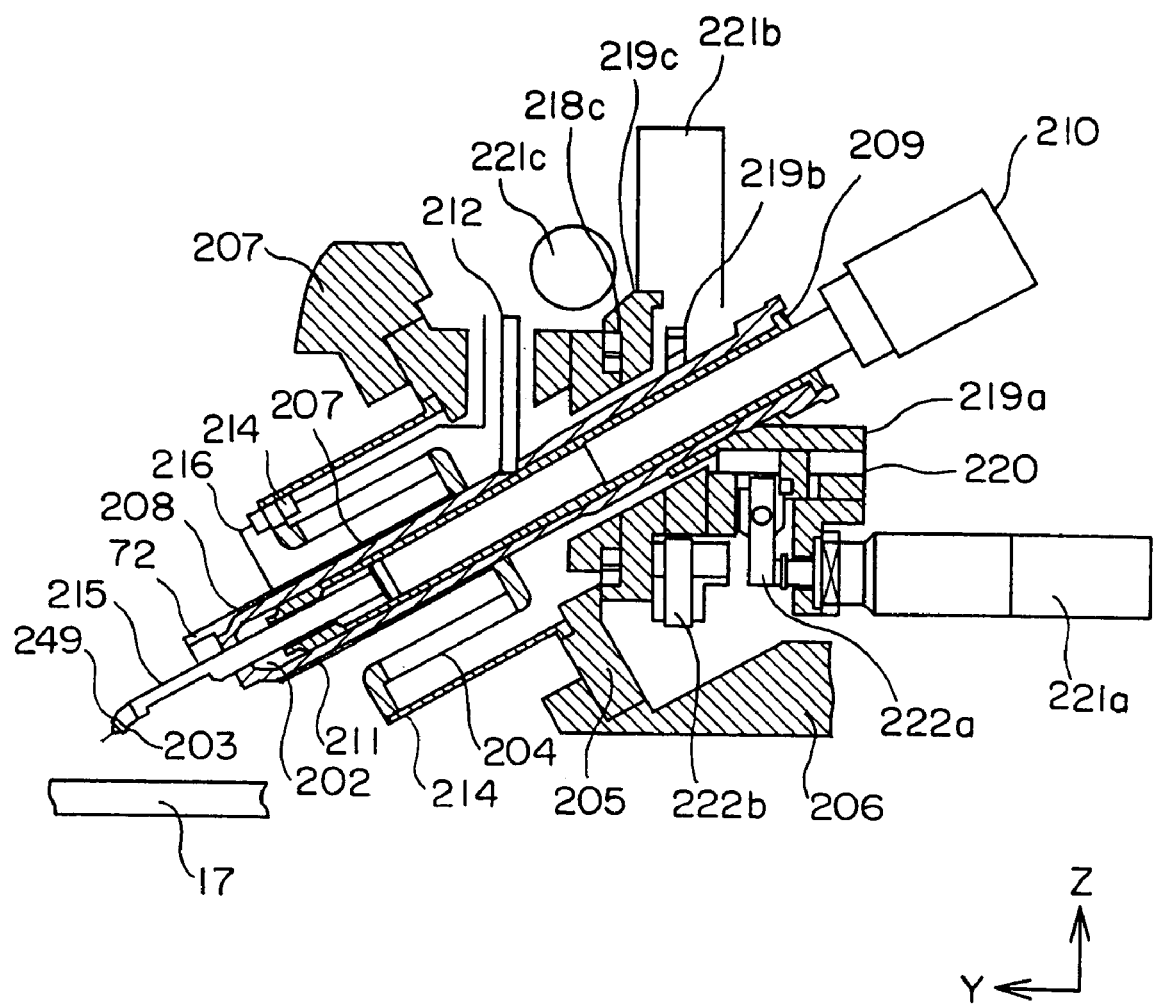
FIG. 17 is a sectional view of a probe moving mechanism for the sample creating apparatus of the fifth embodiment of the present invention.

Details of a probe moving mechanism 201 (manipulator) which is controlled by the probe position controller 223 will be described with reference to FIGS. 17 and 18. An air lock chamber 202 provided in the probe moving mechanism 201 is coupled to a base flange 205 via bellows 204 absorbing a moving amount of a probe 203. The base flange 205 is fixed to a vacuum container 206 with a vacuum seal 207 interposed therebetween. A closable air lock valve 208 is disposed at an end of the air lock chamber 202, and opened/closed by rotating a cylindrical air rock valve opening/closing mechanism 209. Shown in FIG. 17 is a condition where the air lock valve 208 is opened and a probe holder 210 is introduced into the vacuum container 206 in such a manner that its central axis is inclined to a surface of the wafer 217. An air rock chamber outer cylinder 211 in which the air lock valve 208 and air rock valve opening/closing mechanism 209 are accommodated has a concentrical hollow double structure, and one end of the hollow portion communicates with the air lock chamber 202 and the other end communicates with an exhaust pipe 212. The above structure eliminates the need for compact bellows for the air lock chamber 202 which has been conventionally required, permitting simplification, miniaturization and reduction in cost of the probe moving mechanism 201.

On a fixed side flange 213 of the bellows 204, a current introduction terminal 214 having a sealing function is disposed. By connecting via a lead wire 216 a vacuum side of the current introduction terminal 214 to a probe holder 249 which holds the probe 203 and is formed from an insulating material with conduction at portions in contact with the probe 203 and probe holder stopper 215, power can be supplied from an air side to the probe 203.

To one end of the air rock chamber outer cylinder 211, a Y-axis stage 219a is fixed where a Y-axis linear guide 218a is fixed in parallel with the surface of the wafer 217 as shown, and coupled to a Y-axis base 220 via the Y-axis linear guide 218a as shown in FIG. 18. Linear driving of a Y-axis is carried out using a Y-axis linear actuator 221a held by the Y-axis base 220. An output shaft of the Y-axis linear actuator 221a is coupled to a Y-axis stage 219a via a Y-axis lever 222a. The Y-axis base 220 is coupled to a Z-axis stage 219b.

The Z-axis stage 219b is coupled to an X-axis stage 219c via a Z-axis linear guide 218b disposed perpendicularly to the surface of the wafer 217 having a phase 90° different from the Y-axis linear guide 218a as shown. The linear driving of the Z-axis stage 219b is carried out using a Z-axis linear actuator 221b held by the X-axis stage 219c. An output shaft of the Z-axis linear actuator 221b is coupled to the Z-axis stage 219b via a Z-axis lever 222b.

Similarly, the X-axis stage 219c is coupled to the base flange 205 via an X-axis linear guide 218c disposed in parallel with the surface of the wafer 217 having a phase 90° different from the Y-axis linear guide 218a as shown. The linear driving of the X-axis stage 219c is carried out using an X-axis linear actuator 221c held by the base flange 205. An output shaft of the X-axis linear actuator 221c is coupled to the X-axis stage 219c via an X-axis lever 222c.

As described above, coupling the X-, Y- and Z-axes to the respective linear actuators via the respective levers can eliminate projections at the linear actuators and achieve miniaturization of the probe moving mechanism 201. The probe moving mechanism 201 of this embodiment has a width of 172 mm in the X-axis direction and a height of 165 mm in the Z-axis direction which are substantially identical to the width and height of the used linear actuator.

Introduction of the probe holder 210 into the vacuum container 206 according to this embodiment adopts the following procedures. The probe holder 210 is inserted in front of the air lock valve 208. In this condition, the air lock chamber 202 is kept to be sealed by the vacuum seal 207 arranged in an outer cylinder of the probe holder 210. After the insertion, air in the air lock chamber 202 is exhausted to be a vacuum from the exhaust pipe 212 through a hollow portion of the air lock chamber outer cylinder 211. After confirming that a pressure in the air lock chamber 202 reaches a predetermined pressure, the air lock valve 208 is opened using the air lock valve opening/closing mechanism 209, and the probe holder 210 is introduced into the vacuum container 206. The above described operations allow the probe 203 to be introduced into the vacuum container 206 without the vacuum container 206 being exposed to the air.

Extracting the probe holder 210 from the vacuum container 206 can be carried out by the procedure in the reverse order of the insertion. That is, the probe holder 210 is once extracted in front of the air lock valve 208, then the air lock valve 208 is closed using the air lock valve opening/closing mechanism 209. Confirming the closure, the air in the air lock chamber 202 is leaked from the exhaust pipe 212. After confirming an atmospheric pressure, the probe holder 210 is taken out of the probe moving mechanism 201. Adopting the above structure allows replacement of the probe 203 which is a consumable supply to be carried out without the vacuum container 206 being exposed to the air.

As shown in FIG. 16, by structuring the probe holder 210 in such a manner that a substantially central axis of the probe holder 210 enters slantingly to the wafer 217 (in this embodiment, enters at an angle of 30°), the probe holder 210 can reach near the optical axis 224 of the charged particle beam optical system with a minimum length, which permits providing the probe holder 210 with high rigidity and remarkably facilitating handling of the few μm sample piece 232 and operations of making the tip of the probe into contact with a predetermined position on an electron element having a submicron wiring.

Machine parts such as the bellows 204 for absorbing the mounting amount of the probe 203 are not positioned lower than the surface of the wafer 217, so that the probe moving mechanism 201 has no influence on the size of the vacuum container 206, and the vacuum container 206 may be a minimum size determined within a movement range of the wafer 217. Minimizing the vacuum container 206 which determines the size of the apparatus can provide a sample creating apparatus for samples with large diameters mounted with a probe moving mechanism, which permits reduction in occupying area, weight and cost and also miniaturization of exhaust means. In this embodiment, the entering angle of the probe holder 210 is 30°, but not limited to this. The same effect can be obtained by inserting the probe holder 210 slantingly to the vacuum container 206 in such a manner that the probe 203 is within a range of being displayed by the image display apparatus 238.

By arranging the probe moving mechanism 201 in a position where a distance to the intersection point of the center of the base flange 205 which couples the probe moving mechanism 201 to the vacuum container 206 and a vertical line of the optical axis 224 is below ½ of the horizontal movement range of the sample stage 234, below 150 mm in this embodiment, the probe holder 210 can be introduced into the vacuum container 206 with a minimum length at a desired angle, and freedom of a layout of the apparatus can be increased while permitting the vacuum container 206 to be miniaturized. Moreover, by adopting the structure where the respective linear actuators of the probe moving mechanism 201 slantingly entering in the vacuum container 206 and the respective stages are coupled via the levers, the probe moving mechanism 201 can eliminate projections, thus imposing no limitation in the layout to other measurement instruments arranged in the vacuum container 206, preventing problems of unexpected interference or the like and achieving miniaturization of the apparatus.

Creating the sample using this apparatus is carried out by the following procedures. The ion beam 227 emitted from the ion source 225 is focused on a predetermined position on the stage 234 by passing through the optical system 226. The focused ion beam, that is, FIB 227 is spattered in the form of scanning the surface of the wafer 217 to carry out fine processing of the sample piece (not shown). On the stage 234, the wafer 217 and the sample holder 233a for holding the extracted sample piece are placed, and the stage position controller 235 determines a position to be FIB processed and extracted.

The probe 203 mounted on the probe moving mechanism 201 is moved to an extracting position on the wafer 217 independently of the stage 234 by the probe position controller 223. Operations of movement and processing are carried out while observing by scanning with the FIB around the extracting position of the wafer 217 by the FIB controller 236, detecting the secondary electron from the wafer 217 by the secondary electron detector 237, and displaying the obtained secondary particle image on the image display apparatus 238.

For extracting the sample piece, the FIB processing is carried out while changing the attitude of the wafer 217 to cut out the sample piece in the form of a wedge, and deposition gas is supplied to the contact portion of the sample piece where the probe 203 is made into contact with using the deposition gas source 239, and an ion beam assist deposition film is formed to thereby attach the probe 203 to the sample piece. The prove 203 is then raised from the wafer 217 by the probe position controller 223, and moved to a position of the sample holder 233b on the stage 234. The probe 203 is lowered, contact between the wedge portion of the sample piece attached to the probe 203 and the surface of the sample holder 233b is confirmed, and a side surface of the sample piece is attached to the sample holder 233a by the ion beam assist deposition film. The tip of the probe 203 is cut from the sample piece 232 by the FIB and moved to a next sample extracting position by the probe position controller 223.

The above processes make it possible to extract the sample piece 232 at a desired position from the wafer 217 and move it to the sample holder 233b. The above operations are collectively controlled by a central processing unit 240. This embodiment adopts the ion beam assist deposition film as the attaching means between the probe 203 and the sample piece 232, but there is no problem in electrostatic attaching means using an attaching force by static electricity, and the same effect can be obtained as this embodiment in that case. However, attachment by the assist deposition film is desirable for attaching the probe to the accurate position.

In this embodiment, the probe moving mechanism is structured to be slantingly inserted, thereby permitting miniaturization of the sample chamber (vacuum container) in comparison with a probe moving mechanism which is inserted horizontally of the wafer surface disclosed in JP-A-11-56602 specification. For example, when the sample is the semiconductor wafer with the large diameter and the probe moving mechanism is tried to be horizontally introduced, the machine parts such as bellows for absorbing the moving amount of the probe are inevitably positioned lower than the surface of the wafer, therefore the machine parts have to be placed in a position which has no interference with the stage on which the wafer is placed, that is, out of the movement range of the stage. This inevitably causes upsizing of the vacuum container, but the present invention can achieve miniaturization of the vacuum container, and the resultant reduction in an occupying area and cost and miniaturization of a vacuum exhaust pump.

There have been needs for extending the probe from the side wall of the vacuum container to the predetermined position (around the optical axis of the charged particle beam) and thereby providing a long support member for supporting the probe, causing a problem of degraded rigidity. This embodiment can also solve the problem to thereby facilitate positioning the prove in the predetermined position.

(Embodiment 6)

Figure 19:
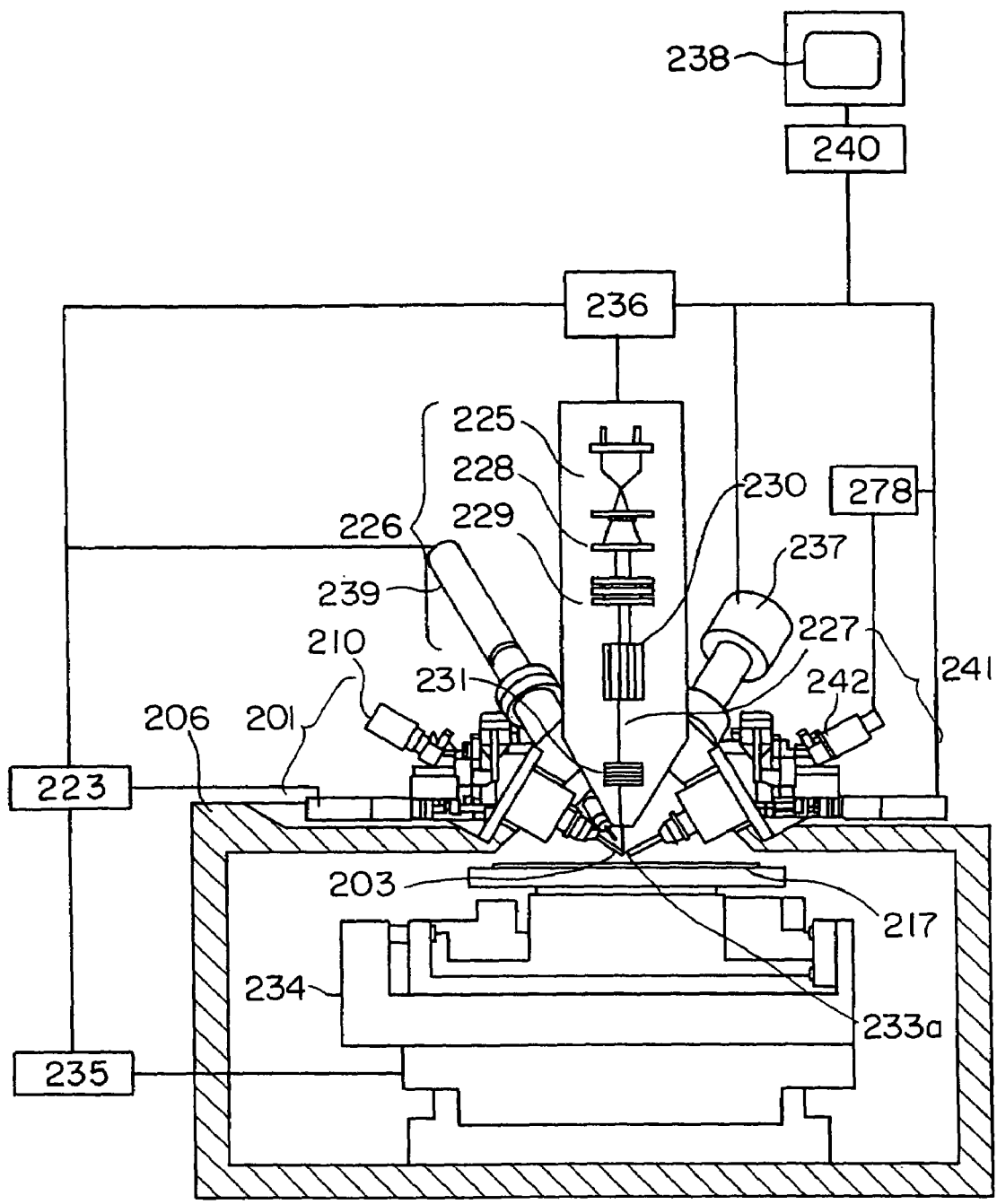
FIG. 19 is a sectional view of a sample creating apparatus of a sixth embodiment of the present invention.
Figure 20:
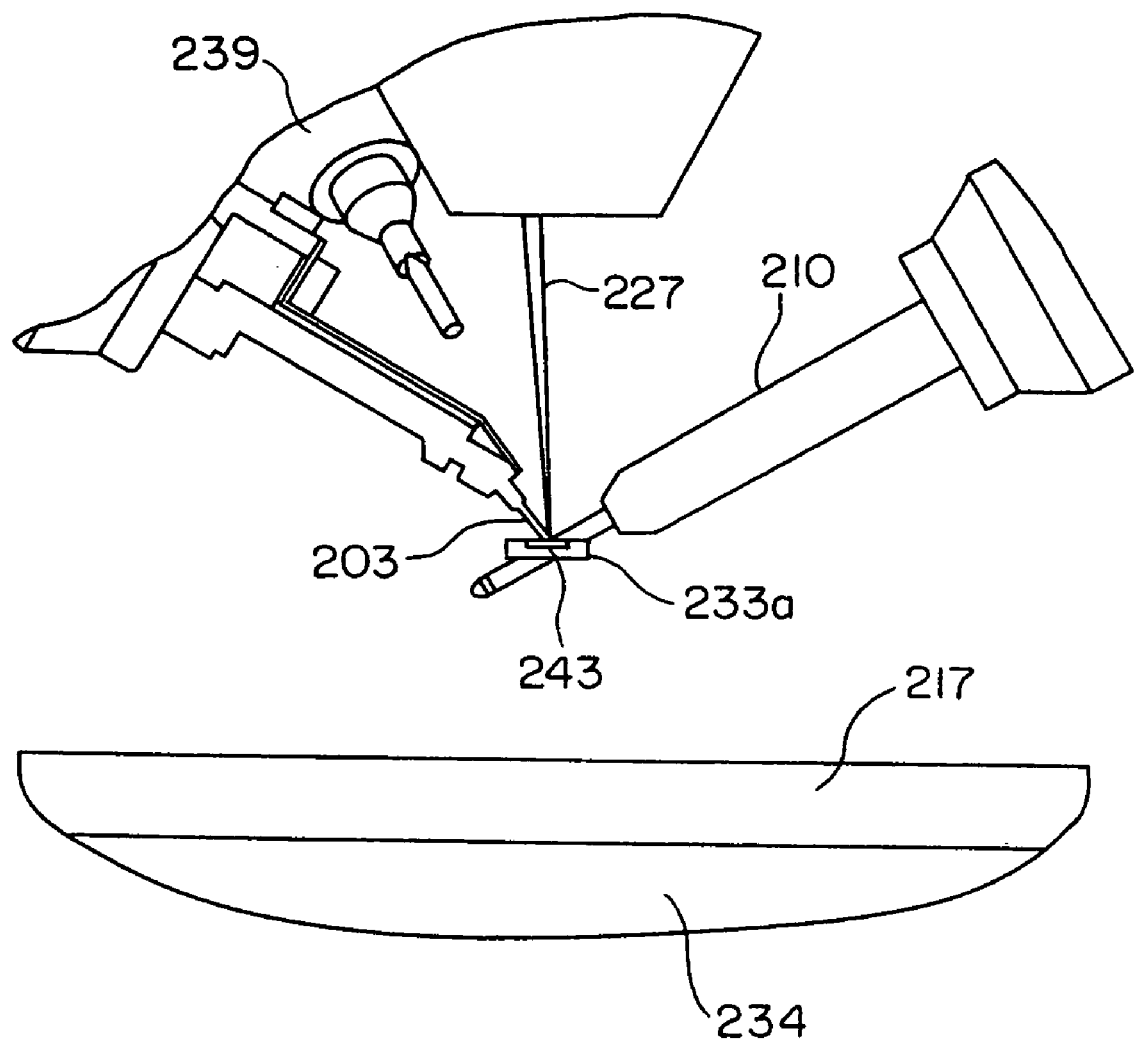
FIG. 20 is an enlarged view of essential portions of the sample creating apparatus of the sixth embodiment of the present invention.
Figure 21A:
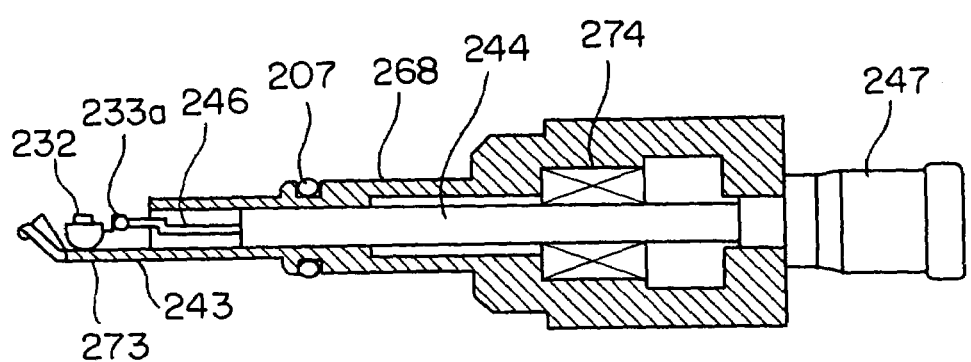
FIG. 21A is a vertical sectional view of a sample stage of the sixth embodiment of the present invention.
Figure 21B:
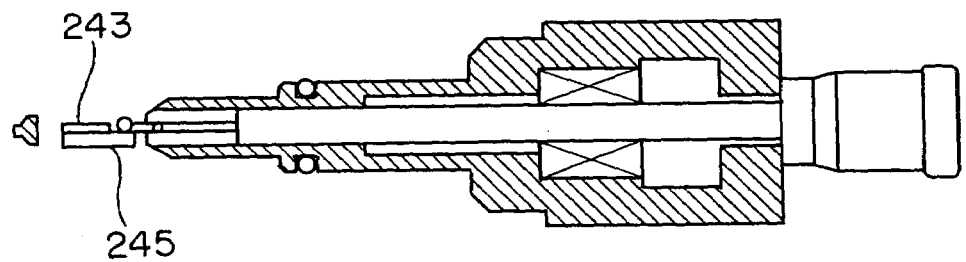
FIG. 21B is a horizontal sectional view of the sample stage of the sixth embodiment.

FIG. 19 is a sectional view of a sample creating apparatus of a sixth embodiment using a slantingly entering sample stage fine moving device 241. Described in the former embodiment has been the example of providing an electron beam barrel in the same sample chamber as the ion beam barrel and observing the sample cut out by the electron beam barrel. However, described in this embodiment is an example of transferring a cut-out sample to other analyzer using a side entry type sample stage and observation is carried out. The side entry type sample stage means a stage to be inserted from the side of a charged particle beam barrel or the sample chamber, and details thereof will be described below. FIG. 20 is an enlarged view of portions around the probe 203 in FIG. 19, and FIG. 21A is a vertical sectional view and FIG. 21B is a horizontal sectional view of a side entry type sample stage 242 used in FIG. 19.

First, the side entry type sample stage 242 will be described with reference to FIG. 21. A sample locating portion 243 to which a sample piece 232 is attached is held by a sample holder 233a. A projection 245 is provided on an end surface of a driving shaft 244 side of the sample holder 233a. The shape of the projection 245 does not matter.

Arranged in a position on an end surface of a vacuum side of the driving shaft 244 is a rotation shaft 246, of which free end is eccentric from a rotational central axis of the driving shaft 244, in contact with a surface of the projection 245 with an attitude in parallel with the central axis of the driving shaft 244. When a knob 247 of the driving shaft 244 is rotated, the rotation shaft 246 is eccentrically rotated and the projection 245 with which the free end of the rotation shaft 246 is in contact is rotationally moved around a rotation bearing 273 depending on an eccentric amount and a rotation amount of the rotation shaft 246. That is, the sample holder 233a is rotationally moved. In this embodiment, rotation at 230° is possible. A part of an outer cylinder 248 of the sample holder 233a portion is cut out and it facilitates attachment of the sample piece 232 to a sample locating portion 243 and forming of the sample piece 232 by the FIB. Using the same mechanical system and control system as the probe moving mechanism 201 shown in FIGS. 17 and 18 for a sample stage fine moving mechanism 241 for driving the side entry type sample stage 242 and a sample stage position controller 278 improves productivity and reduces cost of the apparatus, and also improves maintainability and operability.

Sample creation using the sample creating apparatus according to this embodiment takes the following steps. The operations of introducing and extracting the side entry type sample stage 242 into and from the vacuum container 206 are the same as the operations of the probe holder 210 in the above described probe moving mechanism 201.

Before extraction of the sample piece 232 at a desired position from the wafer 217, the same processes as the fifth embodiment are adopted. After extraction of the sample piece 232, the side entry type sample stage 242 is inserted into the vacuum container 206 without being exposed to the air. In this case, similarly to the fifth embodiment, by structuring the side entry type sample stage 242 in such a manner that a substantially central axis of the side entry type sample stage 242 slantingly enters with respect to the wafer 217, the size of the vacuum container 206 can be minimized, and the side entry type sample stage 242 can reach near an intersection point of the optical axis 224 of the FIB 227 and the wafer 217 with a minimum length. In this embodiment, the side entry type sample stage 242 slantingly enters at an angle of 30° to the surface of the wafer 217, but not limited to 30°. The same effect can be obtained by slantingly inserting the side entry type sample stage 242 into the vacuum container 206 in such a manner that the sample holder 233a exists within a range of being displayed by an image display apparatus 238.

By this structure, for the same reason as the probe moving mechanism 201 in the fifth embodiment, the sample stage fine moving mechanism 241 has no influence on the size of the vacuum container 206 and the vacuum container 206 can be a minimum size which is determined by a movement range of the wafer 217. By arranging the sample stage fine moving mechanism 241 in a position where a distance to an intersection point of a center of the base flange 205 which couples the sample stage fine moving mechanism 241 to the vacuum container 206 and a vertical line of the optical axis 224 is below ½ of the horizontal movement range of the sample stage 234, below 150 mm in this embodiment, the side entry type sample stage 242 can be introduced with a minimum length at a desired angle, and freedom of a layout of the apparatus can be increased while permitting the vacuum container 206 to be miniaturized.

After insertion of the side entry type sample stage 242, the knob 247 is turned to rotate the sample locating portion 243 held by the sample holder 233a at an angle in parallel with the wafer 217 as shown in FIG. 20, that is 30° in this embodiment. Then, the probe 203 holding the sample piece 232 is driven by the probe moving mechanism 201 and a probe position controller 223 shown in FIG. 19, and the minute sample piece 232 is attached to the sample holder 233a by forming a deposition film. After attachment, the sample holder 233a is again rotated to the position in parallel with the axis of the side entry type sample stage 242, and the side entry type sample stage 242 is then extracted from the vacuum container 206 by the above described means, and for example, mounted to a TEM apparatus (not shown) to thereby carry out TEM observation. The rotation of the sample holder 233a is used for fine rotational adjustment of the sample piece 232 in the TEM observation to permit more reliable analysis.

By adopting the structure according to this embodiment, the FIB apparatus can be realized which has the vacuum container 206 with the size restricted to the same size as in the fifth embodiment, the probe moving mechanism 201 which can extract the sample piece 232 at a desired position on the wafer 217 and the side entry type sample stage 242 which can be mounted to various analyzers. By using this FIB apparatus, it becomes possible to transfer the sample piece 232 at a desired position of the wafer 217 with a large diameter to the sample holder 233a in the vacuum container 206, and further, by taking out the side entry type sample stage 242 on which the sample holder 233a is placed without being exposed to the air, prompt mounting on various analyzers and evaluation become possible. Further, by adopting a sample stage fine moving device with the same manner as the probe moving mechanism 201, improvements of productivity, maintainability, and operability of an apparatus can be realized.

(Embodiment 7)

Figure 22:
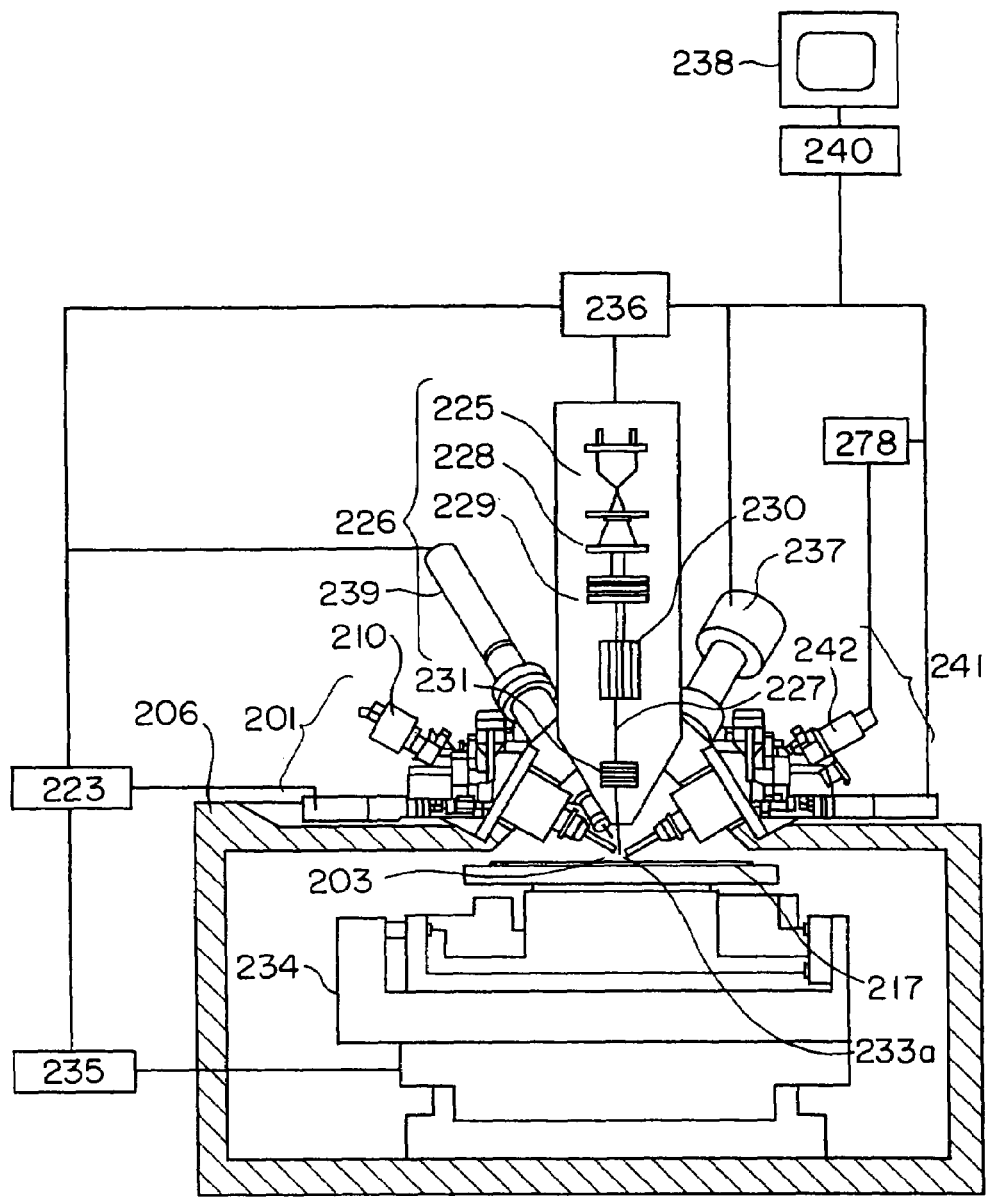
FIG. 22 is a sectional view of a sample creating apparatus of a seventh embodiment of the present invention.

FIG. 22 is a sectional view of a sample creating apparatus of still another embodiment. The embodiment differs from the sixth embodiment in that it uses a probe moving mechanism 201 having a probe holder 210 in which freedom of rotation around a Y-axis shown by the coordinate system shown in FIG. 16 is added to a probe 203 shown in FIG. 23, and a sample stage fine moving mechanism in which freedom of rotation around a central axis of a side entry type sample stage 242 is added to a sample holder 233a shown in FIG. 24.

Figure 23A:
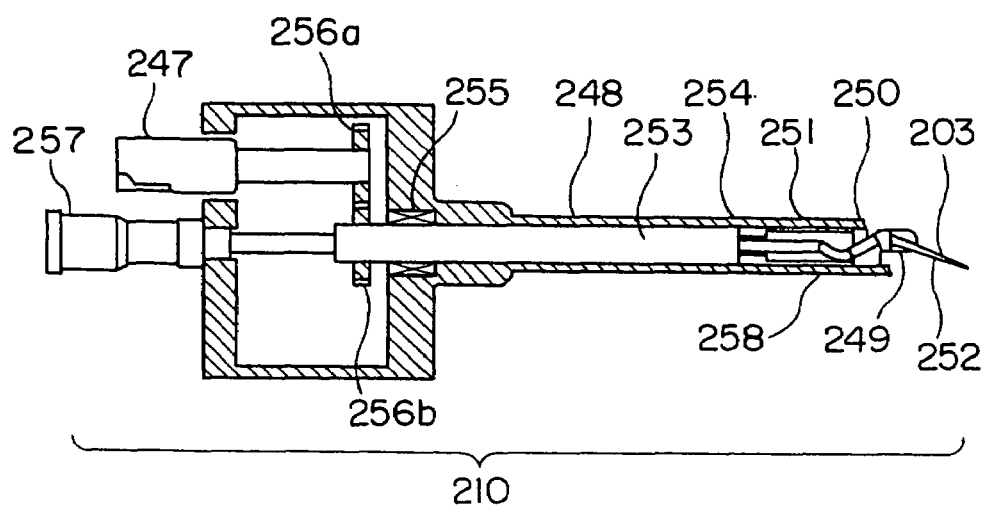
FIG. 23A is a sectional view of a probe holder of the seventh embodiment, showing a condition in which the probe is projected.
Figure 23B:
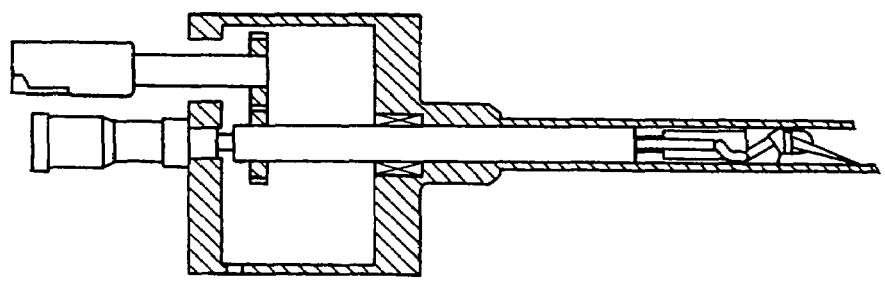
FIG. 23B is a sectional view of the probe holder of the seventh embodiment, showing a condition in which the probe is received.

The structure of the probe holder 210 will be described with reference to FIG. 23. FIG. 23A shows the probe 203 in a projected condition, and FIG. 23B shows the probe 203 accommodated in an outer cylinder 248. The probe 203 is fixed to a probe holder 249 through a leaf spring 252, and the probe holder 249 is held in an inner cylinder 251 which linearly moves through a bearing 250. The inner cylinder 251 is inserted into an outer cylinder 248 with freedom in a rotating direction being limited, and pressed against a driving shaft 253 via a bearing 254. An end of the probe holder 249 is connected to a helical compression spring 259, and the other end of the helical compression spring 259 is coupled to the driving shaft 253. A rotation center of the bearing 250 is inclined to a center line of the probe holder 210 at an insertion angle of the probe holder 210. This allows the probe 203 to be rotationally moved in parallel with the surface of the wafer 217 in the vacuum container 206. If such a probe is applied to the apparatus described in the first embodiment, observation by a scanning electron microscope capable of non destructive observation with high resolution becomes compatible with application substantially in a vertical direction to the sample section. As is the apparatus of the present invention, in an apparatus handling large samples, a probe and a moving mechanism of the probe must be disposed above the samples. However, the probe and the probe moving mechanism disclosed in FIG. 23 permit rotation of a cut out minute sample around a rotation axis parallel to a sample surface.

The driving shaft 253 is inserted into the outer cylinder 248 with a bearing 255 for rotation and linear moving and a vacuum seal (not shown) interposed. An end of the driving shaft 253 projects from the outer cylinder 248. A gear 256b is fixed to the projected portion of the driving shaft 253, and a minute feeding mechanism 257 which is an actuator of linear movement is pressed against an end surface of the driving shaft 253. Another gear 256a in mesh with the gear 256b is arranged in parallel with the driving shaft 253, and a knob 247 for rotary movement is fixed to the gear 256a. It is needless to say that the gears 256a, 256b are held via rotatable members, though not shown. The above is the basic structure of the probe holder 210 having two degrees of freedom of rotation and accommodation of the probe 203.

Next, operations will be described. The driving shaft 253 is linearly moved using the minute feeding mechanism 257. The linear movement of the driving shaft 253 is transferred to the outer cylinder 248, thus the probe 203 held by the probe holder 210 is linearly moved without rotation. By this structure, accidents such as damages of the minute probe 203 can be prevented in operations such as inserting or extracting the fine probe holder 210 into or from the vacuum container 206, and an operator can easily use the apparatus.

The probe 203 is rotationally moved by turning the knob 247, rotationally moving the driving shaft 253 via the gears 256a, 256b. Since freedom of rotation of the inner cylinder 251 is limited, the rotary movement of the driving shaft 253 does not cause rotary movement of the inner cylinder 251. An elastic deformation by the helical compression spring 259 changes a direction of the rotary movement, but the rotary power is transferred to the probe holder 249, and the probe holder 249 held via the inner cylinder 251 and bearing 250 for rotation is rotationally moved. As described above, by simple operations of linear and rotary movements of a single driving shaft 253, the probe 203 can move linearly and rotationally.

Figure 24:
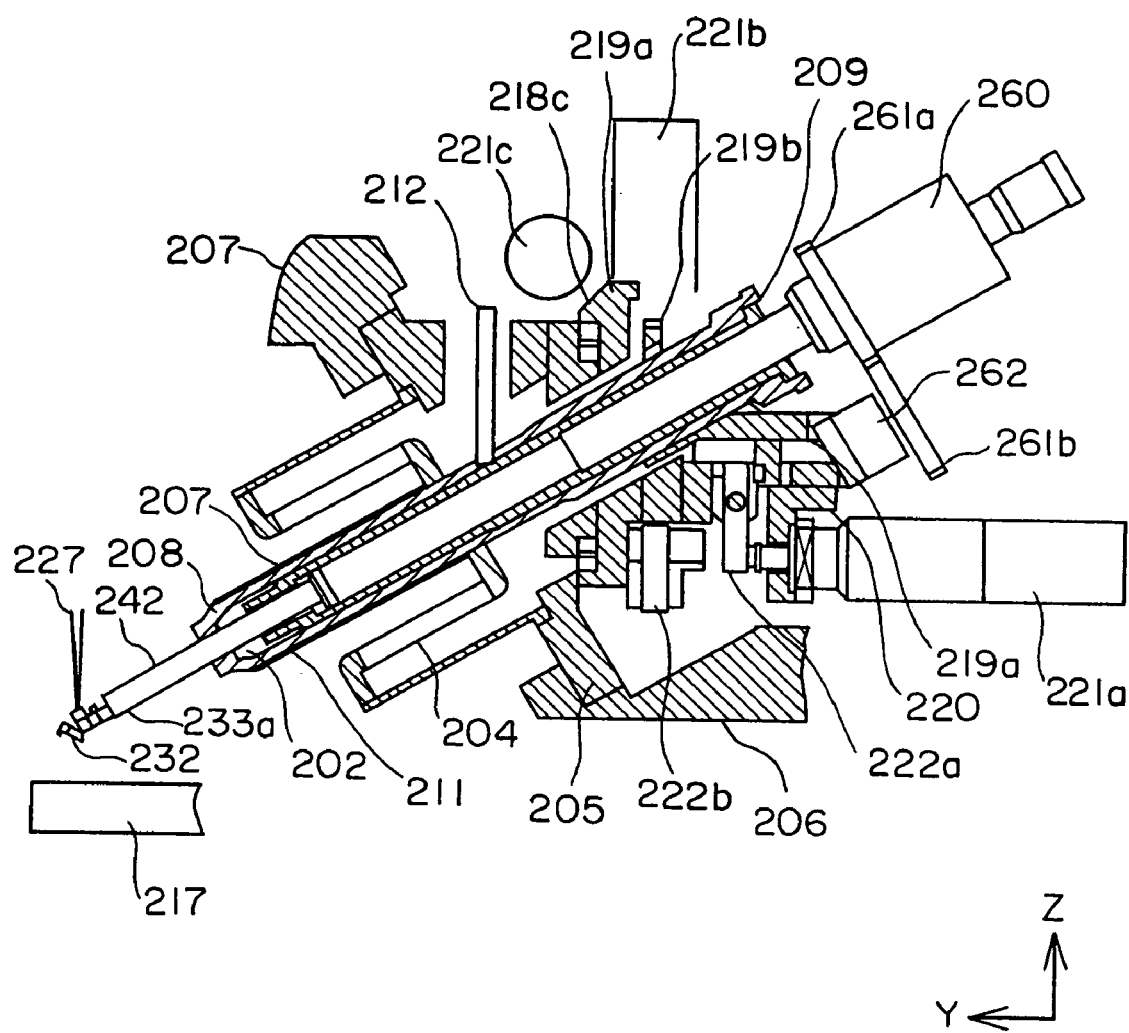
FIG. 24 is a sectional view of a sample stage fine moving mechanism of the seventh embodiment.

Next, the fine moving mechanism of the side entry type sample stage 242 to which freedom of rotation is added will be described with reference to FIG. 24. The respective moving mechanisms of the X-, Y- and Z-axes are of the same type as the probe moving mechanism 201 shown in FIGS. 17 and 18, and only different points will be described below.

In this embodiment, the difference from the sixth embodiment is that a gear 261a is disposed on a grip 260 of a side entry type sample stage 242, and a gear 261b in mesh with the gear 261a and a driving source 262 for rotatably driving the gear 261b are disposed on a Y-axis stage 219a. By the structure of this embodiment, the side entry type sample stage 242 can be inclined at a desired angle by rotationally moving the sample holder 233a portion together with the whole side entry type sample stage 242. Further, by using the gears 261a, 261b as transferring media of the rotary power, the gear 261a coupled to the side entry type sample stage 242 can be coupled to the gear 261b coupled to the driving source 262 using no mechanical parts such as screws with no bars in inserting and extracting the side entry type sample stage 242.

Figure 25:
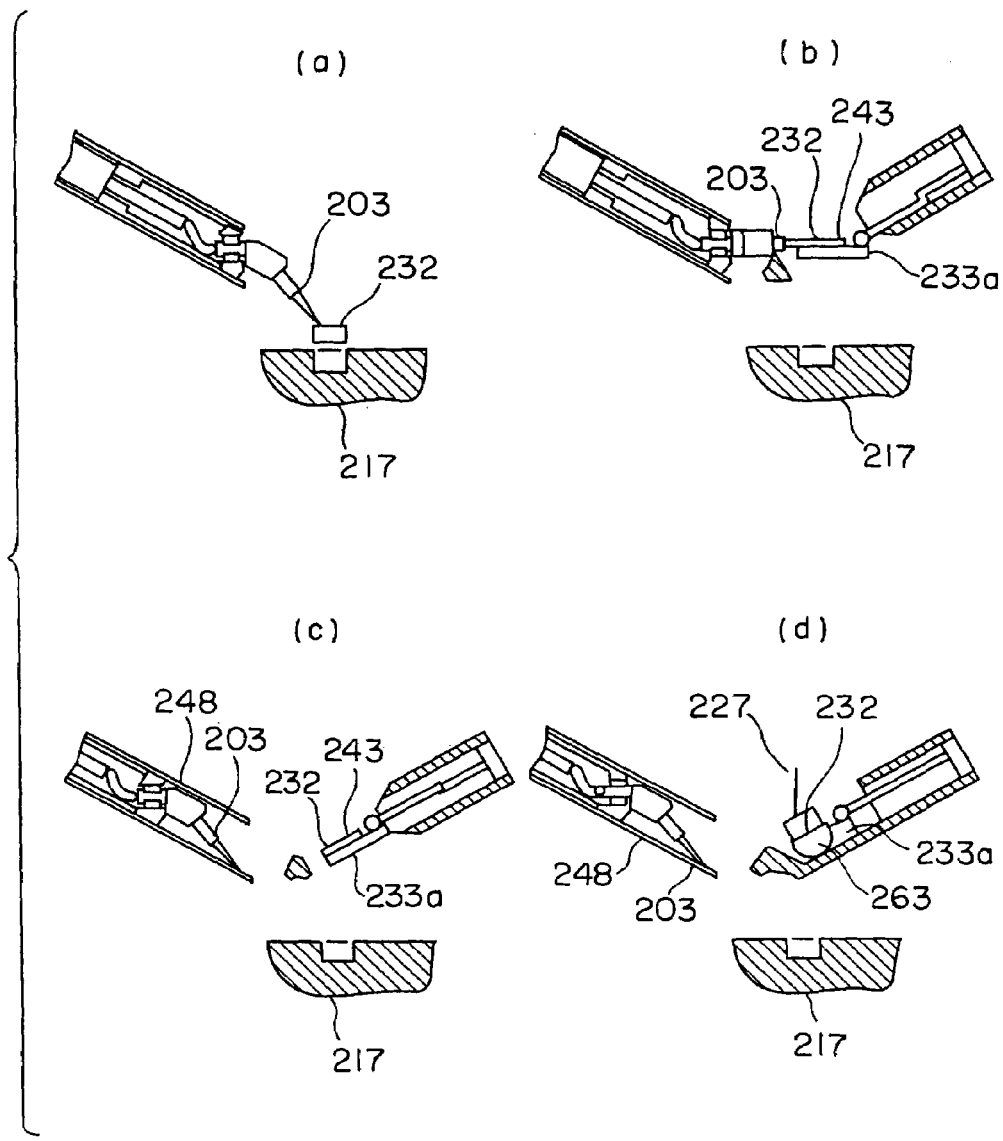
FIG. 25 is views showing processing steps to process a minute sample with the sample creating apparatus of the seventh embodiment.

FIG. 25 shows operations of processing the sample piece 232 by the sample creating apparatus of FIG. 22. Sample creating by the sample creating apparatus of this embodiment will be described with reference to this figure. The same steps as the fifth embodiment are adopted before the step (a) for extracting the sample piece 232 from the wafer 217.

When analyzing an outermost surface of the wafer 217, as described in the sixth embodiment, the sample piece 232 is transferred on a sample locating portion 243 rotationally moved in parallel with the surface of the wafer 217 without rotating the probe 203. When analyzing the wafer 217 in the depth direction, the sample piece 232 is extracted from the wafer 217 and then the probe 203 is rotated at an angle of 90°, and the X-, Y- and Z-axes are driven if necessary, and the sample piece 232 is attached by the ion beam assist deposition film to the sample locating portion 243 which has been rotationally moved in parallel with the surface of the wafer 217 (FIG. 25(b)). After the sample piece 232 is transferred to the sample locating portion 243, the probe 203 is linearly moved using the minute feeding mechanism 257 so as to be accommodated in the outer cylinder 248. Then, the knob 247 is turned to reset the inclined sample holder 233a holding the sample locating portion 243 (FIG. 25(c)). Then, the driving source 262 is driven, and the sample holder 233a is rotationally moved in such a manner that the sample locating portion 243 is opposed to the FIB 227, and the sample piece 232 is forming worked by the FIB 227 (FIG. 25(d)).

In this case, during the steps of processing, by rotating and inclining the sample holder 233a to have a position in FIG. 25(b), it is possible to observe the condition of the observation surface at any time through an image display apparatus 238 for displaying secondary particle images from the sample surface. After forming worked, it is possible to carry out analysis by extracting the side entry type sample stage 242 from the vacuum container 206 and mounting it as it is on an analyzer such as TEM.

According to the sample creating apparatus of this embodiment, analysis of the outermost surface layer and in the depth direction of the wafer 217 is possible, and further, a wide range of sample analyses is possible because of having the same structure as the side entry type sample stage 242 capable of being mounted to various analyzers, thereby greatly enlarging a range of utilization as the sample creating apparatus.

In the above embodiment, description has been made on creation and observation of the TEM sample as an example for convenience in description, but not limited to the TEM. It is apparent that the sample surface can be easily analyzed or observed by configuring the apparatus so as to be mounted to any one of the focused ion beam apparatus, transmission electron microscope, scanning electron microscope, scanning probe microscope, Auger electron spectroscopic analyzer, electron probe X-ray microanalyzer, electronic energy deficiency analyzer, secondary ion mass spectroscope, secondary neutron ionization mass spectroscope, X-ray photoelectron spectroscopic analyzer, or electrical measuring apparatus using a probe.

In the charged particle beam apparatus having the ion beam barrel and electron beam barrel as described in the first embodiment, the ion beam barrel and electron beam barrel are relatively inclined to the sample placing surface of the sample stage. The sample piece is separated from the sample placed on the sample stage by the ion beam, and is joined in an deposited manner by the ion beam and gas to a needle member mounted to the tip of the probe and is extracted. The extracted sample piece is moved below the electron beam rotated such that the electron beam can be applied to a predetermined portion. The secondary electron from the sample may be detected by the detector to obtain a scanning electron microscope image.

In the sample creating apparatus described above, the description has been made specially on the FIB 227 only for convenience in description, but the same effects can be obtained as the present invention even in, for example, a sample creating apparatus using a projection ion beam which is configured by replacing a deflector 230 and objective lens 231 with a mask plate and projection lens, or a sample creating apparatus using a laser beam which is configured by replacing an ion source 225 with a laser source. Moreover, there is no problem of making a sample creating apparatus having a structure in which an optical system of a scanning electron microscope is added to the above described sample creating apparatus. In that case, by using the probe moving mechanism 201 having freedom of rotation around the Y-axis shown in the seventh embodiment of the present invention, it becomes possible to observe the sample piece 232 with high resolution by opposing the sample piece 232 together with the probe to the optical system of the scanning electron microscope after the sample piece is taken out of the wafer 217.

(Embodiment 8)

Figure 26:
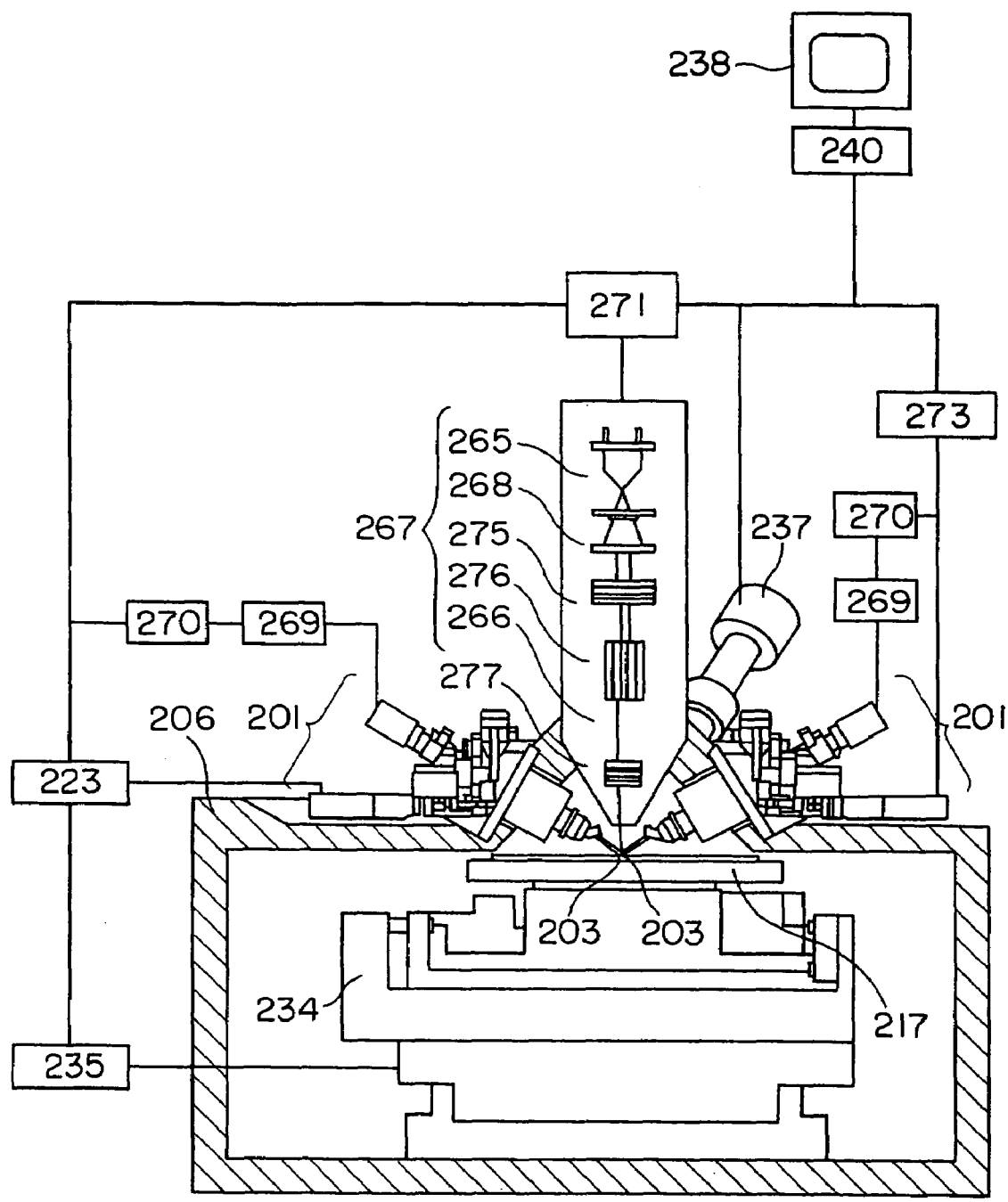
FIG. 26 is a sectional view of a failure inspection apparatus of an eighth embodiment of the present invention.

FIG. 26 is a sectional view of an embodiment where a probe moving mechanism 201 according to the present invention is applied to a failure inspection apparatus. In the figure, an electron beam 266 emitted form an electron gun 265 passes through an electron beam optical system 267 and is focused on a surface of a wafer 217 placed on a stage 234. The stage 234 is controlled by a stage position controller 235 to determine position of an element to be evaluated on the wafer 217. In this figure, only two probe moving mechanisms 201 are shown, but another two probe moving mechanisms 201 are arranged opposite in the direction perpendicular to the sheet surface, thus the failure inspection apparatus is provided with four probe moving mechanisms 201.

A probe 203 arranged in each of four probe moving mechanisms 201 is moved to the position of the evaluation element on the wafer 217 by the probe position controller 223 capable of being driven independently of the stage 234. Movement is carried out with confirming in such a manner that an electron beam controller 271 scans around the evaluation element on the wafer 217 with an electron beam 266, and that a secondary electron from the wafer 217 is detected by a secondary electron detector 237 to display an image of the element portion on an image display apparatus 238.

In this embodiment, a power supply 269 is connected to each probe 203 so that voltage can be applied to a minute portion of the wafer 217 with which applied to a minute portion of the wafer 217 with which the probe 203 comes into contact. At the same time, an amperemeter 270 is also connected to each probe 203 so that a current flowing in each probe 203 can be measured. As an example of an evaluation method, a case in a MOS device formed on the wafer 217 is described. First, three probes 203 are brought into contact with a source electrode, a gate electrode and a drain electrode, respectively. The source electrode is grounded using the probe 203, and while exciting voltage of the gate electrode as a parameter by the probe 203, a relationship between a drain voltage and a drain current flowing between the source and a drain by the probe 203. This provides an output property of the MOS. These operations are collectively controlled by the central processing unit 240.

As the moving mechanism of each probe 203, the probe moving mechanism 201 of the slant entering type shown in FIGS. 17 and 18 is used, so that an inspection of the wafer 217 with a large diameter can be achieved with a compact apparatus. Further, since the structure of probe moving mechanism 201 is one that the replacement or the like of the probe 203 can be easily carried out, and therefore, an operating rate of the apparatus can be improved.

(Embodiment 9)

Figure 27:
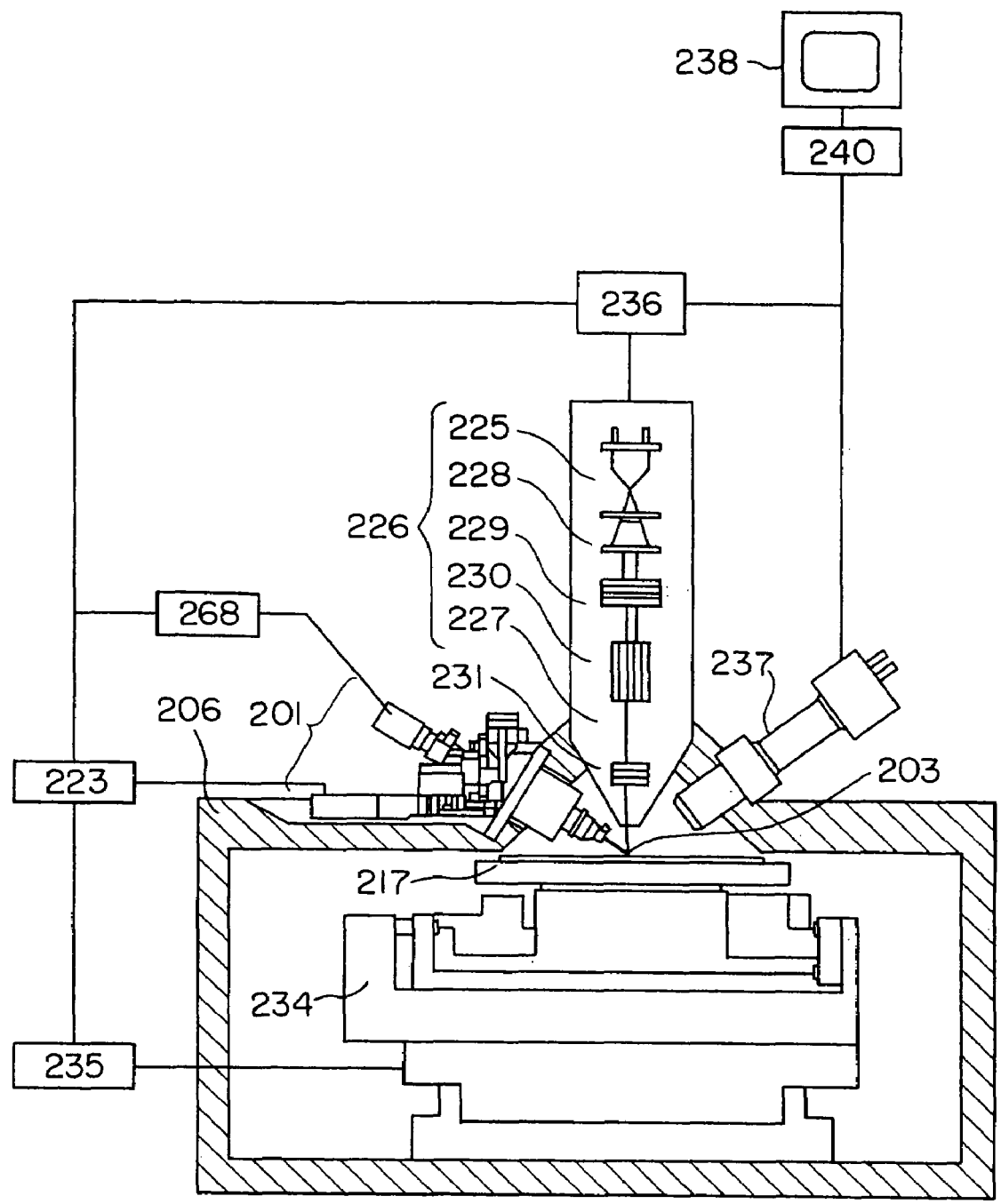
FIG. 27 is a sectional view of a sample observation apparatus of a ninth embodiment of the present invention.

FIG. 27 is a sectional view of a probe moving mechanism 201 of the present invention. In this figure, an FIB 227 emitted from the ion source 225 is focused on a desired position on the stage 234 by passing through an optical system 226. The focused ion beam, that is, FIB 227, is spattered in the form of scanning the surface of the wafer 217 to carry out fine processing. On the stage 234, the wafer 217, semiconductor tip, or the like, are placed and the stage position controller 235 determines an observation position on the wafer 217. The probe 203 mounted on the probe moving mechanism 201 is moved to the observation position on the wafer 217 by the probe position controller 223 which can drive independently of the stage 234. Movement and processing are carried out while observing in such a manner that the FIB controller 236 scans around the observation position on the wafer 217 with the FIB, that a secondary electron from the wafer 217 is detected by a secondary electron detector 237, and that an obtained secondary particle image is displayed on an image display apparatus 238. A power supply 269 is connected to the probe 203 so that voltage can be applied to a minute portion of the wafer 217 with which the probe 203 is brought into contact. In observation, a groove is provided around a circuit by the FIB so as to electrically isolate the circuit to be observed from other circuits. The voltage applied probe 203 is brought into contact with an end of the circuit, and a position is observed which is considered to be connected to the circuit in design. When connected without any break, a contrast is changed (brightened), so that failure of the circuit can be determined. These operations are collectively controlled by the central processing unit 240. As the moving mechanism of the probe, the probe moving mechanism 201 of the slant entering type shown in FIGS. 17 and 18 is used, so that an inspection of the wafer 217 with a large diameter can be achieved with a compact apparatus. Further, since the structure of probe moving mechanism 201 is such that the replacement or the like of the probe 203 can be easily carried out, and therefore, an operating rate of the apparatus can be improved.

The same effects as the present invention can be obtained in, for example, a sample creating apparatus using a projection ion beam which is structure by replacing a deflector 230 and an objective lens 231 with a mask plate and a projection lens, or a sample observing apparatus using a laser beam which is structured by replacing an ion source 225 with a laser source.

What is claimed is:

1. A minute sample processing and observation apparatus comprising:

a first sample stage on which a sample is placed;

a probe for taking out a minute sample from the sample;

a second sample stage on which the minute sample is fixed;

a second sample stage controller that controls an angle of the second sample stage;

a sample chamber in which the first sample stage, the probe and the second sample stage are arranged;

a focused ion beam optical system for applying an ion beam to the sample placed on the first sample stage and the minute sample fixed on the second sample stage;

an electron beam optical system for applying an electron beam to the minute sample fixed on the second sample stage;

wherein the focused ion beam optical system applies the ion beam to the sample placed on the first sample stage for extracting the minute sample from the sample, and the probe supports the minute sample;

the focused ion beam optical system and the electron beam optical system are arranged within the sample chamber;

the minute sample supported by the probe is fixed to the second sample stage;

the focused ion beam optical system applies the ion beam to the minute sample fixed on the second sample stage for creating a desired observation section;

the second sample stage controller controls the angle of the second sample stage so as to locate an observation section at substantially vertical to the electron beam;

the electron beam optical system applies the electron beam to the minute sample for observing the observation section, and observation of an inner section of the sample can be carried out with the sample in the sample chamber, and the sample chamber having a vacuum atmosphere.

2. A minute sample processing and observation apparatus according to claim 1, wherein the sample is a semiconductor device.

3. A minute sample processing and observation apparatus according to claim 1, wherein the sample is a wafer.

4. A minute sample processing and observation apparatus according to claim 1, wherein the minute sample extracted from the sample is a pentahedron.

5. A minute sample processing and observation apparatus according to claim 1, wherein the minute sample extracted from the sample is a tetrahedron.

* * * * *